(12) United States Patent
Endo

(10) Patent No.: US 8,734,856 B2
(45) Date of Patent: May 27, 2014

(54) CELL EXTRACT FOR CELL-FREE PROTEIN SYNTHESIS AND PROCESS FOR PRODUCING THE SAME

(75) Inventor: Yaeta Endo, Matsuyama (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 954 days.

(21) Appl. No.: 10/503,259

(22) PCT Filed: Jan. 31, 2003

(86) PCT No.: PCT/JP03/00975
§ 371 (c)(1),
(2), (4) Date: Nov. 15, 2004

(87) PCT Pub. No.: WO03/064672
PCT Pub. Date: Aug. 7, 2003

(65) Prior Publication Data
US 2005/0064592 A1      Mar. 24, 2005

(30) Foreign Application Priority Data
Jan. 31, 2002 (JP) .................................. 2002-23141

(51) Int. Cl.
*A61K 35/02* (2006.01)
(52) U.S. Cl.
USPC ....................................................... 424/725
(58) Field of Classification Search
None
See application file for complete search history.

(56) References Cited

U.S. PATENT DOCUMENTS

| | | | | |
|---|---|---|---|---|
| 5,434,079 A | * | 7/1995 | Mozayeni | 435/286.5 |
| 5,478,730 A | | 12/1995 | Alakhov et al. | 435/68.1 |
| 5,674,729 A | * | 10/1997 | Wimmer et al. | 435/235.1 |
| 6,399,323 B1 | | 6/2002 | Baranov et al. | 435/68.1 |

FOREIGN PATENT DOCUMENTS

| | | | | |
|---|---|---|---|---|
| EP | 0485608 A1 | 5/1992 | | |
| EP | 0593757 A1 | 4/1994 | | |
| EP | 1477566 A1 | 11/2004 | ............... | C12P 21/00 |
| EP | 1489188 A1 | 12/2004 | ............... | C12P 21/00 |
| JP | 09000291 A | * 6/1995 | | |

OTHER PUBLICATIONS

Pfitzinger et al., Preparation of a tRNA-dependent wheat germ protein-synthesizing system, 1989, Plant Molecular Biology, 12, 301-306.*
Nakano, et al., "An Increased Rate of Cell-free Protein Synthesis by Condensing Wheat-germ Extract with Ultrafiltration Membranes," *Bioscience, Biotechnology, and Biochemistry*, vol. 58, No. 4, pp. 631-634 (1994).
Kigawa et al., "Cell-free production and stable-isotope labeling of milligram quantities of proteins," *FEBS Letters*, vol. 442, No. 1, pp. 15-19 (1999).
Madin et al., "A highly efficient and robust cell-free protein synthesis system prepared from wheat embryos: Plants apparently contain a suicide system directed at ribosomes," *Proc. Natl. Acad Sci. USA*, vol. 97, No. 2, pp. 559-564 (2000).
Szybiak et al., "Control of protein synthesis in a wheat germ cell-free system," *ACTA Biochimica Polonica*, vol. 30, Nos. 3-4, pp. 225-263 (1983).
Kim, et al., "Prolonging cell-free protein synthesis by selective reagent additions," *Biotechnology Progress*, vol. 16, No. 3, pp. 385-390 (2000) (abstract).
Kawarasaki, et al., "Phosphatase-immunodepleted cell-free protein synthesis system," *Journal of Biotechnology*, vol. 61, No. 3, pp. 199-208 (1998).
International Search Report for PCT/JP03/00975, dated Apr. 30, 2003.
International Preliminary Examination Report for PCT/JP2003/000975 (English translation).
Supplemental European Search Report for EP 03 73 4897, dated Mar. 7, 2005.

* cited by examiner

*Primary Examiner* — Amy L Clark
*Assistant Examiner* — Catheryne Chen
(74) *Attorney, Agent, or Firm* — Kilyk & Bowersox, P.L.L.C.

(57) ABSTRACT

The present invention provides a method for preparing cell extract for high-performance cell-free protein synthesis reactions, comprising the elimination of low molecular weight substances that have protein synthesis inhibitory activity, from cell extracts that have cell-free protein synthesis activity, by such methods as dialysis, gel filtration and ultrafiltration. Also provided is a ready-made cell-extract for cell-free protein synthesis employing this method. Furthermore, the formation of insoluble matter can be reduced by performing the process for eliminating the low molecular weight substances that inhibit protein synthesis in the co-presence of ATP, GTP or amino acids, so as to stabilize the cell extract.

16 Claims, 9 Drawing Sheets

(A)

CELL EXTRACT FOR CELL-FREE PROTEIN SYNTHESIS AND PROCESS FOR PRODUCING THE SAME

This application is a National Stage Application of PCT/JP03/00975, filed Jan. 31, 2003, which claims priority from Japanese Patent Application No. 2002-23141 filed Jan. 31, 2002.

TECHNICAL FIELD

The present invention relates to cell extract for use in cell-free protein synthesis, having enhanced protein synthesis reaction activity, and method for preparing the same.

BACKGROUND ART

The development of technologies allowing proteins to be synthesized at will are expected to contribute greatly, not only to the fields of the life sciences and biotechnology, but also to the design of nano-machines and the development of molecular devices in such engineering fields as neural computing. Currently, genetic engineering techniques for introducing cloned DNA into living cells are widely used for protein synthesis, but exogenous proteins that can be produced by these methods are limited to molecules that are able to survive the life support mechanisms of their host. Meanwhile, advances in organic synthesis technology have made automatic synthesizers common, but while peptides comprising a few dozen amino acids are routinely synthesized, chemical synthesis of higher molecular weight proteins is currently extremely difficult, due to limitations in terms of the yield, side reactions, and the like. Furthermore, there has been strong ethical criticism in Europe and the United States of conventional using living organisms to produce proteins, or to search for novel molecules, and there is a concern that international regulations will become even stricter.

Cell-free protein synthesis is a novel protein synthesis method capable of overcoming these problems, which attempts to make maximal use of the outstanding characteristics of living organisms by applying chemical procedures to the same. These methods provide biological systems for the translation of genetic information within artificial containers and, using nucleic acids which have been designed and synthesized as templates, reconstruct systems capable of incorporating the desired amino acids, including those which do not exist in nature. As these systems are not subject to the limitations of living organisms, it can be expected that an almost limitless range of protein molecules can be synthesized.

With regard to cell-free protein synthesis systems, it was reported 40 years ago that pulped cell sap retained the ability to synthesize protein, and various methods of doing this have been developed in the past. Currently, cell extracts derived from *E. coli*, wheat embryo, and rabbit reticulocytes are widely employed in protein synthesis and the like. Cell-free systems allow for rapid translation speeds of 10 peptide bonds per second, which is roughly equal to in vivo translation speeds, and excellent reaction characteristics in terms of translation accuracy, but in all cell-free systems, the period of time for which synthesis can be continued is short and the yield is extremely low, at a few micrograms to a few dozen micrograms per milliliter of reaction volume, which is approximately 1/100 to 1/1000 of the yield of living cells, making this an impractical protein synthesis method.

A major disadvantage of conventional cell-free protein synthesis systems was that synthesis efficiency was extremely low, but no direct studies have been made of the cause. This is because it was common knowledge in the field of biochemistry that activity in cell extracts prepared with artificial buffer from physical ground cells was somewhat lower.

The inventors have already shown, based on the findings of past research into ribosome inactivating toxins, that the extreme drop in protein synthesis activity seen in cell-free protein synthesis systems using wheat embryo extract were the result of a switch for an auto ribosome inactivation mechanism (cell suicide mechanism), which is programmed into the original cell as a defense mechanism against pathogenic microorganisms, and which is triggered by grinding the embryo (Madin, K. et al., *Proc. Natl. Acad. Sci. USA*, 97, 559-564 [2000]). Then, it was demonstrated that protein synthesis reactions using wheat embryo extract that was prepared by a novel method, wherein tritin activity and the like were eliminated from embryo tissues, exhibit good protein synthesis characteristics over a long period of time (Madin, K. et al., *Proc. Natl. Acad.Sci. USA*, 97, 559-564 (2000), JP-2000-236896-A).

However, there are problems with wheat embryo extracts prepared according to such methods in that, depending on the target protein (for example, DNA binding proteins such as transcription factors) by the influence of other inhibition factors meant that it was not always possible to achieve a sufficient yield.

Furthermore, conventional cell extracts for cell-free protein synthesis presented problems in terms of storage stability when solutions that contained the amino acids, energy sources, ions and the like, which are necessary for protein synthesis were added. For this reason, it was necessary to supply the cell extract and the solution containing the energy source and the like separately, requiring that the researcher mix these together with the translation template each time that an experiment was performed. Because of such problems as the necessity of performing these operations at low temperatures, the overall experimental work became difficult, which often caused protein synthesis to fail. Furthermore, such methods for supplying reagents for cell-free protein synthesis reactions are not suited for comprehensive synthesis of proteins from a multiplicity of genes and a major problem facing future robotization is the solution of these problems of complicatedness.

DISCLOSURE OF THE INVENTION

An object of the present invention is to provide a cell extract having enhanced protein synthesis activity so as to improve on procedural complexity, or to improve on low protein synthesis activity for the target protein, in cell-free protein synthesis reactions. Furthermore, in so much as concerns cell-free protein synthesis using wheat embryo extract, an object of the present invention is to provide a cell extract having good storage stability with which, simply by adding the target translation template (mRNA), large volume synthesis and comprehensive protein synthesis, for the purposes of functional and structural analysis of the gene products, can be performed simply and efficiently without the need of preparing a mixed-reaction solution (which is to say, to provide a ready-made cell extract solution).

As a result of earnest study directed at solving the problems described above, the present inventors discovered that by dialyzing wheat embryo extract using a regenerated cellulose membrane having molecular weight cutoff of approximately 12,000 to 14,000 Daltons, low molecular weight substances were removed from the extract and the protein synthesis activity of the cell extract was markedly enhanced. Furthermore, the low molecular weight substances were eliminated by dialysis from a solution containing all of the components necessary for cell-free protein synthesis other than the translation template, the protein synthesis activity of the processed cell extract was enhanced beyond that of conventional cell extracts. Furthermore, as this protein synthesis activity was not decreased, even after storage at −80° C. for four weeks, it was determined that this could be used as a ready-made cell extract.

The present invention was completed based on these observations. That is to say, according to the present invention, (1) A cell extract characterized by having protein synthesis activity and by being free of low molecular weight substance that inhibits protein synthesis.

(2) The cell extract set forth above in (1), wherein the low molecular weight substance that inhibits protein synthesis can be removed by dialysis, using a regenerated cellulose membrane having a molecular weight cutoff of 12,000 to 14,000 Daltons.

(3) The cell extract set forth above in (1), wherein the low molecular weight substance that inhibits protein synthesis is a protein synthesis inhibiting substance having a molecular weight of no greater than 14,000 Daltons.

(4) The cell extract set forth above in any one of (1) to (3), which is substantially free of insoluble matter.

(5) The cell extract set forth above in any one of (1) to (4) characterized in that the cell extract is wheat embryo extract.

(6) A method for preparing cell extract for cell-free protein synthesis characterized by eliminating a low molecular weight substance that inhibits protein synthesis from cell extract having protein synthesis activity.

(7) The method set forth above in (6), wherein the low molecular weight substance that inhibits protein synthesis can be removed by dialysis, using a regenerated cellulose membrane having a molecular weight cutoff of 12,000 to 14,000 Daltons.

(8) The method set forth above in (6), wherein the low molecular weight substance that inhibits protein synthesis is a protein synthesis inhibiting substance having a molecular weight of no greater than 14,000 Daltons.

(9) The method set forth above in any one of (6) to (8), characterized in that the cell extract is wheat embryo extract.

(10) The method set forth above in any one of (6) to (9), characterized in that the protein synthesis inhibiting substance is eliminated by dialysis.

(11) The method set forth above in any one of (6) to (10), characterized in that the elimination of the protein synthesis inhibiting substance is performed in a solution comprising at least a high energy phosphate compound.

(12) The method set forth above in any one of (6) to (11), characterized in that the elimination of the protein synthesis inhibiting substance is performed in a solution comprising components necessary for cell-free protein synthesis, other than a translation template.

(13) The method set forth above in (12) characterized in that the components necessary for protein synthesis are comprised in the solution at concentrations at which cell-free protein synthesis can be performed.

(14) A cell extract for cell-free protein synthesis prepared by the method set forth above in any one of (6) to (13).

(15) A protein synthesis method characterized by using the cell extract set forth above in any one of (1) to (5) or (14).

(16) A kit for performing cell-free protein synthesis characterized by comprising at least the cell extract set forth above in any one of (1) to (5) or (14).

(17) A protein obtained by the method set forth above in (15) or use of the kit set forth above in (16).

DETAILED DESCRIPTION OF THE INVENTION

Figure 1:
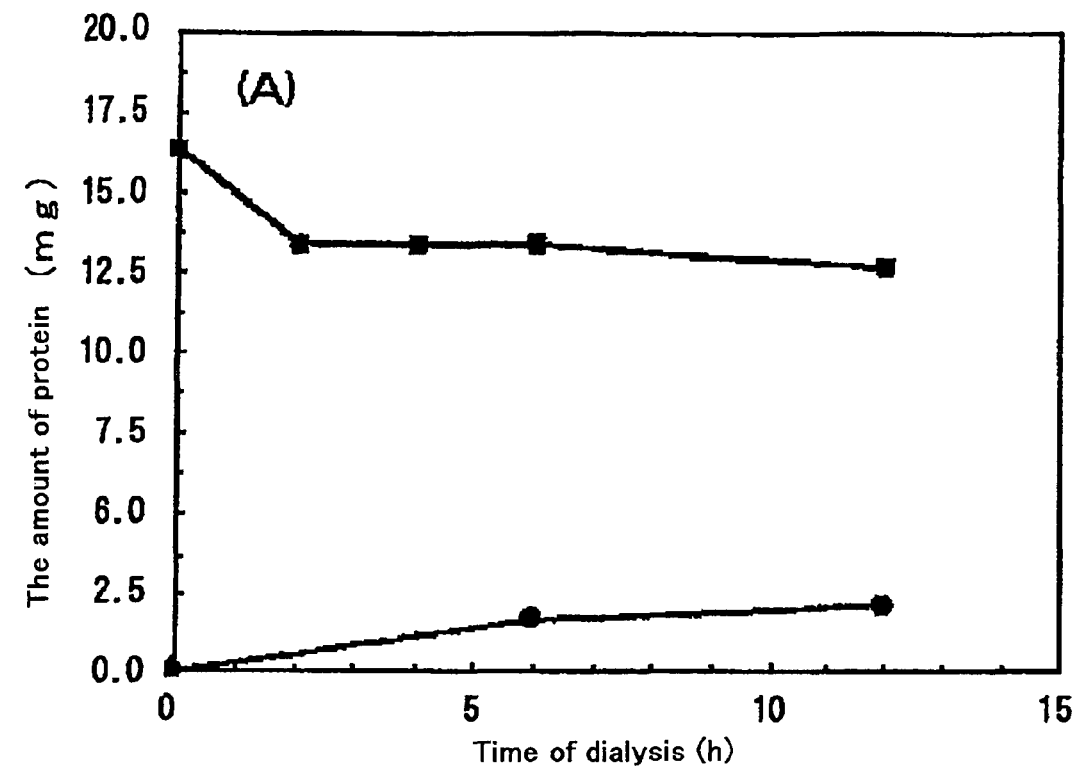
FIG. 1 is a graph showing the formation of insoluble matter due to dialysis of wheat embryo extract and the inhibitory effect of ATP on the same.
Figure 1:
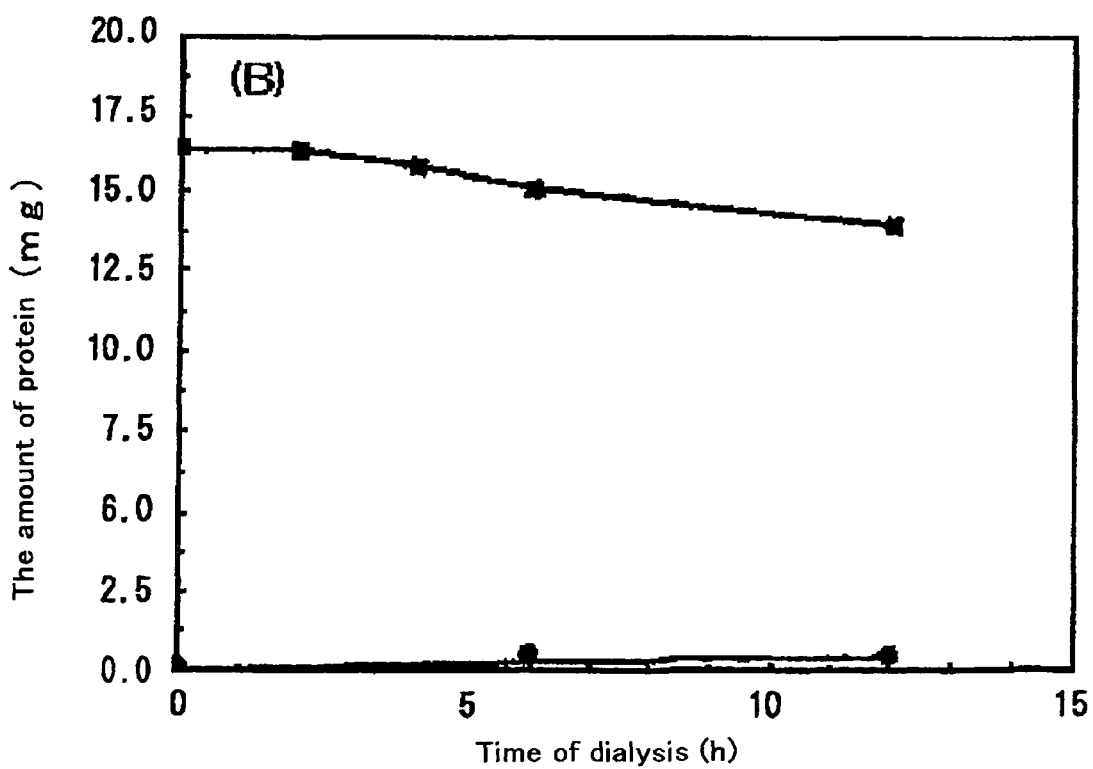

Hereinafter, the present invention is described in further detail.
(1) Elimination of Low Molecular Weight Substances that Inhibit Cell-Free Protein Synthesis Any cell extract may be used to prepare the cell extract for cell-free protein synthesis of the present invention, so long as it has a protein synthesis function in a cell-free protein synthesis system. Herein, the expression "cell-free protein synthesis system" refers to a method performed in vitro, wherein components including ribosomes and the like, which are intracellular protein translation apparatus, are extracted from an organism, and to this extract are added a template for transcription or translation, nucleic acids and amino acids, which serve as substrates, an energy source, various ions, a buffering solution, and other effective factors. These methods include those which use RNA as a template (hereinafter also referred to as "cell-free translation systems") and those using DNA, wherein enzymes necessary to transcription, such as RNA polymerase, are added so as to perform the reaction (hereinafter also referred to as "cell-free transcription/translation systems"). The cell-free protein synthesis system of the present invention includes both the aforementioned cell-free translation systems and the aforementioned cell-free transcription/translation systems.

Specific examples of cell extracts that can be used in the present invention include known cell extracts, such as those from *E. coli*, plant seed embryo, and rabbit reticulocytes.

Commercially available cell extracts may be used, or these may be prepared according to methods such as that described in Pratt, J. M. et al., *Transcription and Translation*, Hames, 179-209, B. D. & Higgins, S. J., eds, IRL Press, Oxford (1984) about cell extract from *E.coli* in particular.

Commercially available cell extracts include *E. coli* S30 extract system (PROMEGA) and RTS 500 Rapid Translation System (ROCHE) and the like, which are derived from *E. coli*, Rabbit Reticulocyte Lysate System (PROMEGA) and the like, which are derived from rabbit reticulocytes, and PROTEIOS™ (TOYOBO) and the like, which are derived from wheat embryo. From among these, the use of plant seed embryo extracts is preferred, and the seeds of members of the Gramineae family, such as wheat, barley, rice, and corn, are preferred as plant seeds. From among these, the use of wheat embryo extract is suitable as the cell extract of the present invention.

Methods for preparing wheat embryo extract include, for example, the method described in Johnston, F. B. et al., *Nature*, 179, 160-161 (1957), or Erickson, A. H. et al,. *Meth. In Enzymol.*, 96, 38-50 (1996) and the like, but a more detailed description is given hereinafter.

Ordinarily, the embryo component is extremely small and therefore, in order to obtain the embryo in an efficient manner, it is preferable that components other than embryo be removed to as great an extent as is possible. Normally, mechanical force is first applied to the plant seeds so as to produce a mixture comprising embryo, crushed endosperm and crushed seed coat. The crushed endosperm, crushed seed coat and the like are removed from this mixture, so as to produce a crude embryo fraction (a mixture primarily composed of embryo but also containing crushed endosperm and crushed seed coat). It suffices that the force applied to the plant seed be of a strength sufficient to separate the embryo from the plant seed. Specifically, a mixture containing embryo, crushed endosperm and crushed seed coat is produced by grinding plant seed using well-known grinding equipment.

The plant seeds can be ground using commonly known grinding apparatus but it is preferable to use grinding apparatus of the type that applies impact force to the material that is ground, such as a pin mill or a hammer mill. The degree of grinding may be suitably chosen according to the size of the embryo of the plant seed that is used. For example, wheat grain is usually ground to a maximum length of no greater than 4 mm, and is preferably ground to a maximum length of no greater than 2 mm. Furthermore, it is preferable that the grinding be performed as dry grinding.

Next, a crude embryo fraction is recovered from the ground plant seed produced, using classifier that is well-known per se, such as a sieve. For example, in the case of wheat grain, a crude embryo fraction is normally recovered using a mesh sieve of 0.5 to 2.0 mm, and preferably 0.7 to 1.4 mm. Furthermore, if necessary, the seed coat, the endosperm, dust and the like contained in the crude embryo fraction produced can be removed using wind force or electrostatic force.

It is also possible to produce a crude embryo fraction using methods that make use of the difference in the specific gravities of embryo, seed coat and endosperm, such as heavy media separation. In order to obtain a crude embryo fraction containing a greater quantity of embryo, a plurality of the methods described above may be combined. Furthermore, it is possible to select the embryo from the crude embryo fraction produced either visually or using a color sorter, or the like.

As an endosperm component may adhere to the embryo fraction produced in this manner, it is normally preferable that this be washed in order to purify the embryo. It is preferable that this be washed by dispersing/suspending the embryo fraction in cold water, a cold aqueous solution, or an aqueous solution containing a surface active agent, that is normally no greater than 10° C. and preferably no greater than 4° C., and washing until the washing solution is no longer clouded. It is more preferable that the embryo fraction be dispersed/suspended in an aqueous solution containing a surface active agent, which is normally at a temperature of no more than 10° C. and preferably at a temperature of no more than 4° C., and washed until the washing solution is no longer clouded. It is preferable that the surface active agent be nonionic, and a wide variety of surface active agents can be used so long as these are nonionic. Specific examples of suitable substances include BRIJ, TRITON, NONIDET P40, TWEEN, and the like, which are polyoxyethylene derivatives. From among these, NONIDET P40 is the most suitable. These nonionic surface active agents can be used at concentrations sufficient to remove the endosperm component, but which do not negatively impact the protein synthesis activity of the embryo component. For example, a concentration of 0.5% can be used. The washing treatment may be either one of washing with water or an aqueous solution, or washing with a surface active agent. Alternatively, the two may be used together. Furthermore, this washing may be combined with an ultrasound treatment.

In the present invention, after selecting the plant embryo from the ground product, which was produced by grinding the plant seed as described above, the intact (capable of germinating) embryo produced by washing is minced (preferably, in the presence of an extracting solvent) whereafter the wheat embryo extract that has been produced is separated and further purified to produce a wheat embryo extract for cell-free protein synthesis.

An aqueous solution comprising buffer solution, potassium ions, and magnesium ions, and/or a thiol antioxidant may be used as the extracting solvent. Furthermore, calcium ions and L-amino acids may be added as necessary. For example, solutions comprising N-2-hydroxyethylpiperazine-N'-2'-ethanesulfonic acid (HEPES)-KOH, potassium acetate, magnesium acetate, L-amino acids and/or dithiothreitol and a solution produced by partially modifying the method of Patterson et al. (solutions comprising HEPES-KOH, potassium acetate, magnesium acetate, calcium chloride, L-amino acids and/or dithiothreitol) can be used as the extracting solvent. The compositions and concentrations of the various components in the extracting solvent are already known per se, and compositions and concentrations commonly used in the preparation of wheat embryo extracts for cell-free protein synthesis may be adopted.

The embryo is mixed with an amount of extracting solvent sufficient for extraction thereof and the embryo is minced in the presence of the extracting solvent. In terms of the amount of extracting solvent used for each gram of unwashed embryo, this is normally no less than 0.1 ml, preferably no less than 0.5 ml, and more preferably no less than 1 ml. There is no particular upper limit on the amount of extracting solvent, but this is normally no more than 10 ml, and preferably no more than 5 ml, for each gram of unwashed embryo. Furthermore, in terms of the embryo which is to be minced, this may be frozen as conventional, or an unfrozen embryo may be used, but the use of unfrozen embryo is preferred.

The embryo may be minced by using a conventional well-known method, such as milling or crushing, as the embryo grinding method, but a method of mincing embryo by impact or chopping (Japanese patent application No. 2002-023139), which was developed by the present inventors, is preferred.

Herein, the expression "mince by impact or chopping" means breaking down the plant embryo under conditions that minimize, as compared to conventional milling or crushing, the breakdown of parts of the plant embryo such as cellular membranes, cell walls, and organelles thereof, such as mitochondria, chloroplasts and the cell nucleus.

There are no particular restrictions on the apparatus and methods that can be used in mincing the embryo, so long as the conditions described above are satisfied, but it is preferable that devices having a high-speed rotary blade, such as a WARING blender, be used. The speed of the rotating blade is normally no less than 1,000 rpm and preferably no less than 5,000 rpm, but this is normally no greater than 30,000 rpm, and preferably no greater 25,000 rpm. The running time for the rotating blade is normally no less than five seconds and preferably no less than 10 seconds. There is no particular upper limit on the running time, but this is normally no more than 10 minutes and preferably no more than five minutes. The temperature during mincing is preferably no greater than 10° C. and is within a temperature range in which the mincing operation is possible. On the order of 4° C. is particularly preferable.

As a result of mincing the embryo by impact or chopping in this manner, the cell nucleus and cell walls of the embryo are not completely destroyed, but rather at least some portion thereof remains without having been broken down. That is to say, as such parts of the embryo as the cellular membranes, cell walls and organelles such as the cell nucleus are not broken down to a greater degree than is necessary, it is possible to efficiently extract substances necessary to protein synthesis, such as RNA, ribosomes and the like, which are localized within the cytoplasm, at high degrees of purity, without contamination by impurities contained therein, such as lipids and DNA.

According to such a method, the conventional step of grinding the plant embryo and the conventional step of mixing the wheat embryo which has been grinded with an extracting solvent are carried out simultaneously, whereby wheat embryo extract can be produced efficiently. The method described above is sometimes referred to hereinafter as the "blender method."

It is preferable that such mincing of the plant embryo, and in particular mincing by impact or chopping, be performed in the presence of an extracting solvent, but it is also possible to add the extracting solvent after mincing.

Next, the wheat embryo extract is recovered by centrifugation or the like and purified by gel filtration or the like, allowing for the production of wheat embryo extract. Gel filtration may, for example, be performed using gel filtration apparatus which has been pre-equilibrated with a suitable solution. The compositions and concentrations of the various components in the gel filtration solution are already known per se, and compositions and concentrations commonly used in the preparation of wheat embryo extracts for cell-free protein synthesis (for example, a solvent containing HEPES-KOH, potassium acetate, magnesium acetate, dithiothreitol, or L-amino acids) may be adopted.

It is preferable that the cell extract obtained in this manner have extremely low RNase activity and phosphatase activity.

Following gel filtration, the solution containing embryo extraction product may be contaminated with microorganisms, and in particular, with spores such as those of filamentous bacteria (mold). It is, therefore, preferable that these microorganisms be eradicated. The proliferation of microorganisms is particularly observed in long-term (more than one day) cell-free protein synthesis reactions. It is, therefore, important to prevent this. There are no particular restrictions on the means for eradicating microorganisms, but the use of antimicrobial filters is preferred. There are no particular restrictions on the pore size for the filter, so long as this is a size capable of eradicating microorganisms with which the cell extract may be contaminated, but 0.1 to 1 µm is normally suitable and 0.2 to 0.5 µm is preferred. It is of note that the spore size of *Bacillus subtilis*, which is of the small class, is 0.5 µm×1 µm and therefore the use of a 0.20 micrometer filter (for example the Minisart™ by Sartorius) is effective in removing spores. When filtering, it is preferable that a filter having a large pore size be used first, whereafter a filter having a pore size capable of eliminating microorganisms by which the cell extract may be contaminated is used.

The cell extract obtained in this manner is purified so as to substantially completely remove endosperm, which comprises substances, contained or retained by the source cell itself, which inhibit protein synthesis function ( substances that act on mRNA, tRNA, translation factor proteins, ribosomes and the like so as to inhibit the function thereof such as tritin, thionine, ribonuclease, and the like). Herein, the expression "purified so as to substantially completely remove endosperm" refers to wheat embryo extracts from which endosperm components have been removed to an extent that ribosomes are substantially not deadenylated. Furthermore, the expression "to an extent that ribosomes are substantially not deadenylated" means that the ribosome deadenylation is less than 7%, and preferably less than 1%.

Even when the preferred mincing method described above is employed, such cell extract may contain a certain amount of low molecular weight substances that inhibit protein synthesis (hereinafter, these are sometimes referred to as "low molecular weight synthesis inhibitors"). Therefore, these low molecular weight synthesis inhibitors are removed from the constituent components of the cell extract, based on differences in molecular weight. It suffices that the molecular weight of the substances to be eliminated (low molecular weight synthesis inhibitors) be less than that of the factors contained within the cell extract that are necessary to protein synthesis, but this may vary depending on the type of method used to eliminate these low molecular weight synthesis inhibitors, as described below. For example, if the low molecular weight synthesis inhibitors are eliminated by dialysis using a regenerated cellulose membrane having a molecular weight cutoff of approximately 12,000 to 14,000 Daltons, this would be the molecular weight of the substances eliminated by this dialysis, and specific examples would be molecular weights of no greater than 14,000 to 50,000 Daltons, and preferably no greater than 14,000 Daltons.

Commonly used methods, which are well-known per se, can be used as the method for eliminating the low molecular weight synthesis inhibitors from the cell extract, and specific examples include methods based on dialysis by way of a dialysis membrane, gel filtration, ultrafiltration and the like. In the present invention, the expression "free of" low molecular weight synthesis inhibitors means free of low molecular weight synthesis inhibitors to as great an extent as is true for solutions having been processed by the various methods described above so as to eliminate low molecular weight synthesis inhibitors, and whether or not these have been eliminated can be verified by way of the amount of protein synthesis activity in the cell extract produced.

Methods based on dialysis (dialyzing) are preferred for such reasons as the ease of supplying the substance to the internal dialysis solution. Hereinafter, an example of the use of dialysis is described in detail.

Examples of dialysis membranes which can be used for dialysis include those having molecular weight cutoff of 12,000 to 50,000 Daltons. Specifically, the use of a regenerated cellulose membrane having a molecular weight cutoff of 12,000 to 14,000 Daltons (Viskase Sales, Chicago) and the SPECTRA/PORE 6 (Spectrum Laboratories Inc., CA, USA) having a molecular weight cutoff of 50,000, is preferred. A suitable amount of the aforementioned cell extract is placed within such a dialysis membrane and dialysis is performed according to normal methods. It is preferable that the period of time for which dialysis is performed be on the order of 30 minutes to 24 hours.

(2) Inhibiting the Formation of Insoluble Matter (Stabilizing the Cell Extract)

When the low molecular weight synthesis inhibitors are eliminated, in cases where insoluble matter forms in the cell extract, by means of inhibiting this (hereinafter also referred to as "stabilizing the cell extract") it is possible to increase the protein synthesis activity of the final cell extract (hereinafter also referred to as "processed cell extract"). Herein, insoluble matter is matter recovered as a precipitate from the cell extract in a process for eliminating low molecular weight synthesis inhibitors under suitable conditions, and specifically, by centrifuging, filtering or the like and particularly centrifuging at approximately 10,000 to 80,000 xg, and preferably 30,000 xg, for approximately 5 to 60 minutes, and preferably 20 minutes.

Specific methods for stabilizing the cell extract include methods wherein the elimination of the low molecular weight synthesis inhibitors described above in (1) is performed in a solution containing at least high energy phosphate compounds, such as ATP, GTP and the like. The use of ATP as the high-energy phosphate compound is preferred. Furthermore, it is preferable that this be performed in a solution containing ATP and GTP, and more preferably ATP, GTP and the 20 types of amino acids.

When the low molecular weight synthesis inhibitors are eliminated in a solution containing these components (hereinafter also referred to as "stabilizing components"), the stabilizing components may be added to the cell extract beforehand and supplied to the process for eliminating low molecular weight synthesis inhibitors after incubation. If dialysis is used for the elimination of low molecular weight synthesis inhibitors, the low molecular weight synthesis inhibitors can be eliminated by dialyzing with stabilizing components added not only to the cell extract, but also to the external dialysis solution. Adding a stabilizing component to the external dialysis solution is preferable as, even if the stabilizing component is broken down during dialysis, new stabilizing component is continuously supplied. This can also be applied when gel filtration or ultrafiltration is used, and the same effect can be achieved by equilibrating the various carriers with a filteration buffer solution containing a stabilizing component, whereafter a cell extract containing the stabilizing component is supplied and filtration is performed by adding the above buffer solution.

The amount of stabilizing component to be added and the time for the stabilization treatment may be suitably chosen according to the type of cell extract and the preparation method. Methods for selecting the same include those wherein various different amounts and types of stabilizing component are experimentally added to the cell extract and, after a suitable amount of time, the process for eliminating low molecular weight synthesis inhibitors is performed, whereafter the soluble fraction and the insoluble fraction are separated by such methods as centrifuging the processed cell extract obtained, and the stabilizing component for which the least amount of insoluble matter was formed is chosen. Furthermore, a method is also preferred wherein the processed cell extracts obtained are used to perform cell-free protein synthesis, and a cell extract having high protein synthesis activity is chosen. Furthermore, the selection methods described above also include methods wherein, in cases where dialysis is used for the process of eliminating low molecular weight synthesis inhibitors, suitable stabilizers are added to the external dialysis solution and dialysis is performed for a suitable period of time using these, whereafter selection is made according to the amount of insoluble matter in the cell extract, the protein synthesis activity of the cell extract produced, and the like. It is preferable that the amount of insoluble matter contained in the cell extract, which has been subjected to stabilization processing, be lowered.

In so much as regards the cell extract of the present invention, the expression "substantially free of" insoluble matter means that the insoluble matter has been removed to as great an extent as is true for solutions having been processed by the various methods described above so as to eliminate low molecular weight synthesis inhibitors, and whether or not these have been eliminated can be verified by the amount of protein synthesis activity in the cell extract produced.

Specific examples of stabilization conditions for cell extracts selected in this manner include, in the case of performing process for eliminating low molecular weight synthesis inhibitors by way of dialysis with the wheat embryo extract prepared using the blender method as described in (1), adding 100 µM to 0.5 mM of ATP, 25 µM to 1 mM of GTP and 25 µM to 5 mM of each of the 20 types of amino acid and dialyzing for 30 minutes to one hour or more. If dialysis is used, this may be performed at any temperature, so long as it is a temperature that does not impair protein synthesis activity, and at which dialysis is possible. Specifically, the minimum temperature is a temperature at which the solution does not freeze, normally $-10°$ C and preferably $-5°$ C., and the maximum temperature is the limit for avoiding negative impact on the solution used for dialysis, which is $40°$ C. and preferably $38°$ C.

There are no particular restrictions on the method for adding the stabilizing component to the cell extract, but this may be added before the process for eliminating low molecular weight synthesis inhibitors, incubated for a suitable period of time so as to achieve stabilization, whereafter the process for eliminating low molecular weight synthesis inhibitors may be performed. Alternatively the process for eliminating low molecular weight synthesis inhibitors may be performed using a cell extract to which the stabilizing component has been added and/or using a buffer solution to which this stabilizing component has been added for the purpose of use in this elimination process.

The cell extract of the present invention may be stored in any state, including preferably as cell extract that has undergone dialysis processing and, particularly preferably, cell extract that is substantially free of insoluble matter, and may be stored at low temperatures: preferably no greater than $-20°$ C. and more preferably no greater than $-80°$ C. It is particularly preferable that this be stored in a freeze-dried state. As described below, when used as a ready-made cell extract, storage in a freeze-dried state is particularly preferable, as protein synthesis can be performed simply by dissolving this at the time of use and adding a translation template.

(3) Cell-Free Protein Synthesis

The cell extract from which low molecular weight synthesis inhibitors have been removed, which was obtained in this manner, can be introduced into various selected systems and apparatus that are known per se, allowing protein synthesis to be performed. Systems and apparatus for protein synthesis include the batch method (Pratt, J. M. et al, *Transcription and*

*Translation*, Hames, 179-209, B. D. & Higgins, S. J., eds, IRL Press, Oxford [1984]), wherein method of energy sources and amino acids necessary for cell-free protein synthesis, or tRNA, are added to the cell extract, or the continuous cell-free protein synthesis system (Spirin, A. S., et al., *Science*, 242, 1162-1164 (1988)), the dialysis method (Kikawa et al., 21st Meeting of The Molecular Biology Society of Japan, WID6), or the overlay method (WO 00/68412), which continuously supply the amino acids, the energy source and the like to the reaction system. Furthermore, such methods may be used as those wherein the template RNA, the amino acids, the energy source and the like are added to the synthesis reaction system when necessary and the synthesis products and decomposed matters are removed when necessary (JP-2000-333673-A, hereinafter sometimes referred to as "discontinuous gel filtration").

As the reaction stops when protein synthesis is performed over a long period of time, using the batch method, from among these methods, the use of systems in which amino acids and an energy source are continuously provided, or discontinuously provided, which allows the reaction to be maintained over a long period of time, makes further increases in efficiency possible. Here, when wheat embryo extract is prepared by the blender method, as described above in (1), as this contains a sufficient amount of tRNA, it is not normally necessary to add tRNA.

When protein synthesis is performed by way of the batch method, for example, the synthesis reaction solution described above, without a translation template, is pre-incubated for a suitable period of time as necessary, whereafter the translation template is added and protein synthesis is performed by incubation and the like. If wheat embryo extract is used, the pre-incubation is at 10 to 40° C. for 5 to 10 minutes and the incubation is likewise at 10 to 40° C., preferably 18 to 30° C., and more preferably 20 to 26° C. The reaction time is the time until the reaction stops, and in the batch method this is normally on the order of 10 minutes to 7 hours.

If protein synthesis is performed by means of the dialysis method, the synthesis solution is used as the internal dialysis solution and a device is used whereby this is separated from the external dialysis solution by a dialysis membrane, through which substances can travel, whereby protein synthesis is performed. Specific examples include those wherein the synthesis reaction solution described above, without a translation template, is pre-incubated for a suitable period of time as necessary, whereafter the translation template is added, whereafter this is placed in a suitable dialysis chamber as the internal reaction solution. Examples of the dialysis chamber include containers having a dialysis membrane at the bottom (DIALYSIS CUP 12,000 and the like produced by Daiichi Pure Chemicals Co., Ltd.), dialysis tubes (12,000 and the like, produced by Sanko Junyaku Co., Ltd). The dialysis membrane used may have a molecular weight cutoff of 10,000 Daltons or more, those with a molecular weight cutoff on the order of 12,000 Daltons being preferred.

The aforementioned synthesis reaction solution, without the template, is used as the external dialysis solution. It is possible to improve dialysis efficiency by replacing the external dialysis solution with fresh dialysis solution when the reaction speed drops. The reaction temperature and time are suitably selected according to the protein synthesis system to be used, but in systems wherein wheat embryo extract is used, this is normally performed at 10 to 40° C., preferably 18 to 30° C., and more preferably 20 to 26° C., for 10 minutes to twelve days.

When the protein synthesis is carried out using the overlay method, the synthesis reaction solution is placed in a suitable container, and the external dialysis solution described above in the dialysis method is overlaid on top of this solution(the synthesis reaction solution) so as not to disturb the interface, so as to carry out the protein synthesis. Specific examples include those wherein the synthesis reaction solution described above, without the translation template, is pre-incubated for a suitable period of time as necessary, whereafter the translation template is added, whereafter this is placed in a suitable container as the reaction phase. Examples of the container include a microtiter plate or the like. The external dialysis solution described above in the dialysis method (supply phase) is overlaid on the top layer of this reaction phase so as not to disturb the interface, so as to carry out the reaction.

In addition, the interface between the two phases does not have to be formed by superposition in a horizontal plane; a horizontal plane can also be formed by centrifuging a mixture that contains both phases. When the diameter of the circular interface between the two phases is 7 mm, a volume ratio of the reaction phase and the supply phase of 1:4 to 1:8 is adequate, and 1:5 is optimal. The rate of exchange of substances due to diffusion increases with the area of the interface formed by the two phases, increasing the protein synthesis efficiency. Therefore, the volume ratio of the two phases changes according to the area of the interface between the two phases. The synthesis reaction is carried out under static conditions, and the reaction temperature and time are suitably selected for the protein synthesis system to be used, but in systems using wheat embryo extract is performed at 10 to 40° C., preferably 18 to 30° C. and more preferably at 20 to 26° C., normally for 10 to 17 hours. Furthermore, when *E. coli* extract is used, a reaction temperature of 30 to 37° C. is suitable.

When the protein synthesis is carried out using the discontinuous gel filtration method, the synthesis reaction is performed by way of the synthesis reaction solution, and when the synthesis reaction stops, the template RNA, the amino acids, the energy source and the like are supplied, and the products of synthesis or degradation are evacuated, so as to carry out the protein synthesis. Specific examples include those wherein the synthesis reaction solution described above, without a translation template, is pre-incubated for a suitable period of time as necessary, whereafter the translation template is added, whereafter this is placed in a suitable container and the reaction is performed. Examples of the container include a microtiter plate or the like. In this reaction, when, for example, the reaction solution contains 48% by volume of wheat embryo extract, the synthesis reaction stops completely in one hour. This can be verified by measuring the incorporation of amino acids into protein or by analysis of polyribosomes by centrifugation over a sucrose density gradient (*Proc. Natl. Acad. Sci. USA*, 97, pp. 559-564 [2000]).

The reaction solution in which the synthesis reaction has stopped is passed through a gel filtration column, which has been pre-equilibrated with a supply solution that has the same composition as the external dialysis solution described in the dialysis method above. The synthesis reaction is resumed by re-incubating the filtered solution at a suitable reaction temperature, and the protein synthesis proceeds over several hours. Thereafter, these reaction and gel filtration operations are repeated. The reaction temperature and time are suitably selected according to the protein synthesis system to be used, but in systems in which wheat embryo extract is used, it is preferable that gel filtration be repeated approximately every hour at 26° C.

The proteins obtained in this way can be identified by a method known per se. Specific examples include: measurement of amino acids incorporated into proteins; separation by SDS-polyacrylamide electrophoresis and staining with Coomassie brilliant blue (CBB); autoradiography (Endo, Y., et al., *J. Biotech.*, 25, 221-230 [1992]; *Proc. Natl. Acad. Sci. USA.*, 97, 559-564 [2000]) and the like.

Furthermore, as the reaction solution produced in this manner contains a high concentration of the target protein, the target protein can easily be obtained from the reaction solution by separation and purification methods well-known per se, such as dialysis, ion exchange chromatography, affinity chromatography, gel filtration, and the like.

(4) Ready-Made Cell Extract for Cell-Free Protein Synthesis

A ready-made cell extract can be prepared by performing the process for eliminating low molecular weight synthesis inhibitors described above in (1) or (2), and the cell extract stabilization process for this process, in a solution containing all of the components necessary for a cell-free protein synthesis, other than the translation template. What constitutes all of the components necessary for cell-free protein synthesis, other than the translation template, will vary depending on the origin of the cell extract used, and on whether the cell-free protein synthesis of the present invention is a cell-free translation system or a cell-free transcription/translation system. In the case of a wheat embryo cell-free translation system, this comprises at least the amino acid and the energy sources (ATP and GTP) as substrates, and in the case of a cell-free transcription/translation system, in addition to the components mentioned above, the nucleic acid as substrates and the RNA polymerase are necessary. Specifically, in the case of a wheat embryo cell-free translation system, it is preferable that this comprise, in addition to the amino acid as substrate and the energy sources, at least one of: various ions, buffer solution, an ATP regenerating system, a nuclease inhibitor, tRNA, a reducing agent, polyethylene glycol, 3',5'-cAMP, folate, an antimicrobial agent, or the like. In terms of specific concentrations, it is preferable that the ATP be at 100 µM to 0.5 mM, the GTP be at 25 µM to 1 mM, and that each of the 20 types of amino acid be at 25 µM to 5 mM. Other components may likewise be contained at the concentrations commonly used in the art. Here, if a wheat embryo extract prepared according to the blender method described above in (1) is used as the cell extract, it is not normally necessary to add tRNA.

(5) Reagents and Kits

The cell extract for cell-free protein synthesis of the present invention, and preferably the processed cell extract and the ready-made cell extract, may be provided to a kit for cell-free protein synthesis reactions containing the same. In the case of a cell extract for a cell-free protein synthesis or a processed cell extract, the kit of the present invention comprises, in addition to these, those components necessary or suitable for the protein synthesis system and specifically, the amino acid as substrate and the energy sources, various ions, buffer solution, an ATP regenerating system, a nuclease inhibitor, tRNA, a reducing agent, polyethylene glycol, 3',5'-cAMP, folate, an antimicrobial agent and the like, surface active agents, RNA polymerase, translation template nucleic acids for positive control, vectors for constructing translation templates, reaction containers, and the like. Furthermore, in the case of a ready-made cell extract, as this contains all of the components necessary or suitable for the protein synthesis system, it also contains other substances. However, it is not necessary that all of these reagents be included, and any combination of reagents may be included so long as this constitutes a kit that can be used for cell-free protein synthesis.

EXAMPLES

In the following, the present invention is described in further detail by way of examples, but the following examples are only intended to aid in concrete appreciation of the present invention, and the scope of the present invention is in no way limited to the examples described below.

Example 1

Preparation of Wheat Embryo Extract

Hokkaido Chihoku wheat grain (undisinfected) was added to a mill (FRITSCH: Rotor Speed Mill Pulverisette 14) at a rate of 100 g per minute, and the grain was moderately ground at a rotation speed of 8,000 rpm. After recovering a fraction containing germinatable embryos with a sieve (mesh size 0.7 to 1.00 mm), the surfacing fraction containing the germinatable embryos was recovered by flotation using a mixture of carbon tetrachloride and cyclohexane (volume ratio=carbon tetrachloride:cyclohexane=2.4:1), the organic solvent was eliminated by desiccation at room temperature, and then impurities such as seed coat were eliminated by air-blowing at room temperature to obtain a crude embryo fraction.

Next, a belt type color sorter BLM-300K (Manufacturer: Anzai Manufacturing Co., Ltd., Marketed by Anzai Co., Ltd.) was used to select the embryo from the crude embryo fraction by way of color difference, in the following manner. This color sorter is a device comprising: means for irradiating the crude embryo fraction with light; means for detecting reflected light and/or transmitted light from the crude embryo fraction; means for comparing the detected value with a reference value; and means for selecting or eliminating that which is outside the standard value or that which is within the standard value.

The crude embryo fraction was supplied onto the color sorter belt so as to produce 1,000 to 5,000 particles/m$^2$, the crude embryo fraction on the belt was irradiated with fluorescent light, and the reflected light was detected. The belt transport speed was 50 m/minute. A monochrome CCD line sensor (2,048 pixels) was used as the photosensor.

First, in order to eliminate components darker than the embryo (seed coat and the like), a beige colored belt was used, the standard value was set between the brightness of the embryo and seed coat, and objects outside of the standard value were removed by suctioning. Next, in order to select the endosperm, a dark green belt was used, the standard value was set between the brightness of the embryo and endosperm, and objects outside of the standard value were removed by suctioning. Suctioning was performed by way of 30 suction nozzles (the suction nozzles were aligned with one suction nozzle for each centimeter of length) positioned approximately 1 cm above the transport belt.

By repeating this process, the embryo was selected to a embryo purity (weight ratio of embryo per gram in any sample) of no less than 98%.

The wheat embryo fraction obtained was suspended in distilled water at 4° C., and washed using ultrasonic washing apparatus until the washing solution was no longer clouded. This was then suspended in a 0.5% (volume) NONIDET (Nacalai Tectonics) P40 solution and washed using an ultrasonic washing apparatus until the washing solution was no longer clouded, so as to obtain the wheat embryo whereafter operations were performed at 4° C.

Two volumes of extracting solvent (80 mM of HEPES-KOH (pH 7.8), 200 mM of potassium acetate, 10 mM of magnesium acetate, 8 mM of dithiothreitol, (0.6 mM of each of the 20 kinds of L-amino acids may be added)) were added with respect to the wet weight of the washed embryo, and the embryo was subject to limited grinding in a WARING blender for three cycles of 30 seconds each, at 5,000 to 20,000 rpm. The centrifugation supernatant obtained from this homogenate by centrifuging in a high-speed centrifuge for 30 minutes at 30,000×g was centrifuged again under the same conditions, and the supernatant was collected. The activity of this sample was not observed to drop with long term storage at −80 or less °C. The supernatant collected was passed through a filter having a pore size of 0.2 μm (NEW Steradisc 25: Kurabo Industries Ltd.) so as to sterilize it by filtration sterilization and remove micro contaminants.

Next, gel filtration was performed using a SEPHADEX G-25 column (AMERSHAM Pharmacia Biotech) that had been pre-equilibrated with a solution (consisting of 40 mM of HEPES-KOH (pH 7.8), 100 mM of potassium acetate, 5 mM of magnesium acetate, 4 mM of dithiothreitol and 0.3 mM of each of the 20 types of L-amino acids (depending on the protein synthesis objective, amino acids may be omitted or labeled amino acids may be added)). The resulting filtrate was once again centrifuged for 30 minutes at 30,000×g and the density of the supernatant recovered was adjusted so that the A260 nm was 90 to 150 ($A_{260}/A_{280}$=1.4-1.6), after which it was stored at −80 or less ° C. until it was used in the dialysis and protein synthesis reaction described below.

Example 2

Elimination of Low Molecular Weight Substances From Wheat Embryo Extract and Analysis of Protein Synthesis Reaction Activity (1) Fractionation with Dialysis Membrane The wheat embryo extract prepared in Example 1 contained factors necessary for protein synthesis (tRNA, aminoacyl-tRNA synthetases, ribosomes, translation initiation factors, peptide chain elongation factors, translation termination factors, and the like) and other molecules such as, in particular, substances that inhibit protein synthesis in a specific or nonspecific manner. An attempt was, therefore, made to fractionate these by exploiting the differing molecular weights thereof, so as to prepare a wheat extract from which substances inhibiting protein synthesis had been eliminated.

A dialysis membrane was used for the fractionation. A SPECTRA/PORE 6 (Spectrum Laboratories Inc., CA, USA) having a molecular weight cutoff of 50,000 was used as the dialysis membrane. This molecular weight cutoff was selected as being capable of preventing the passage of factors necessary to protein synthesis while fractionating molecules having molecular weights lower than this.

The wheat embryo extracts supplied to dialysis were prepared: as an extract solution 1 which was used in a protein synthesis reaction and therefore did not contain ATP, GTP or amino acids (wheat embryo extract [prepared in example 1] constituting two thirds of the total volume, 30 mM of HEPES-KOH(pH 7.6), 95 mM of potassium acetate, 2.65 mM of magnesium acetate, 2.85 mM of dithiothreitol, 0.380 mM of spermidine, 1,000 units/ml of ribonuclease inhibitor (RNase inhibitor), 16 mM of creatine phosphate, and 0.5 mg/ml of creatine kinase); or as an extract solution 2 wherein 1.2 mM of ATP were added to the extract solution 1.

Dialysis was performed at 26° C. or at 4° C. under static conditions for 12 hours using the extract solutions described above, and an external dialysis solution equivalent to 50 volumes of the extract solution, and having exactly the same composition as the extract solutions, but not containing the embryo extract. These internal dialysis solutions (extract solutions) were sampled over time and the amount of precipitate resulting from centrifugation was analyzed as a measure of protein synthesis activity, and of the stability of the extract solutions. Analysis of the component eliminated by the dialysis membrane was also performed.

(2) Analysis of Extract Solution Stability

Samples were taken from the extract solutions undergoing dialysis in (1) once every hour for 12 hours and these were centrifuged for 20 minutes at 20,000×g. The amounts of protein contained in the soluble fraction, obtained as the supernatant, and the insoluble fraction, obtained as the precipitate, were measured by the Bradford method, using bovine serum albumin as standard, and the results are shown in FIG. 1. FIG. 1(A) shows the results for the extract solution 1 (no ATP) and (B) shows the results for extract solution 2 (ATP added). The line indicated by the solid square shows the amount of protein in the soluble fraction, and the line indicated by the solid circle shows the amount of protein in the insoluble fraction. Protein amounts are shown for 1 ml of extract solution.

As shown in FIG. 1, with the extract solution 1, which did not contain ATP, GTP or amino acids, two hours after dialysis was started, a sudden drop in soluble protein concentration was observed, whereafter this reached a substantially constant value, and 12 hours after dialysis was started the concentration was 77.5% of the concentration at the beginning. Conversely, the amount of insoluble protein increased, whereby it was understood that this drop in soluble protein concentration was primarily due to insolubilization of protein occurring during dialysis. Furthermore, with the extraction solution 2, to which ATP had been added, the rate at which the downward curve for soluble protein concentration dropped was moderate, and the proportion of insoluble proteins was low, with soluble proteins representing 85.3% after 12 hours. From these results it can be asserted that the addition of ATP limits insolubilization of wheat embryo extract during dialysis and improves the stability of this solution.

Figure 2:
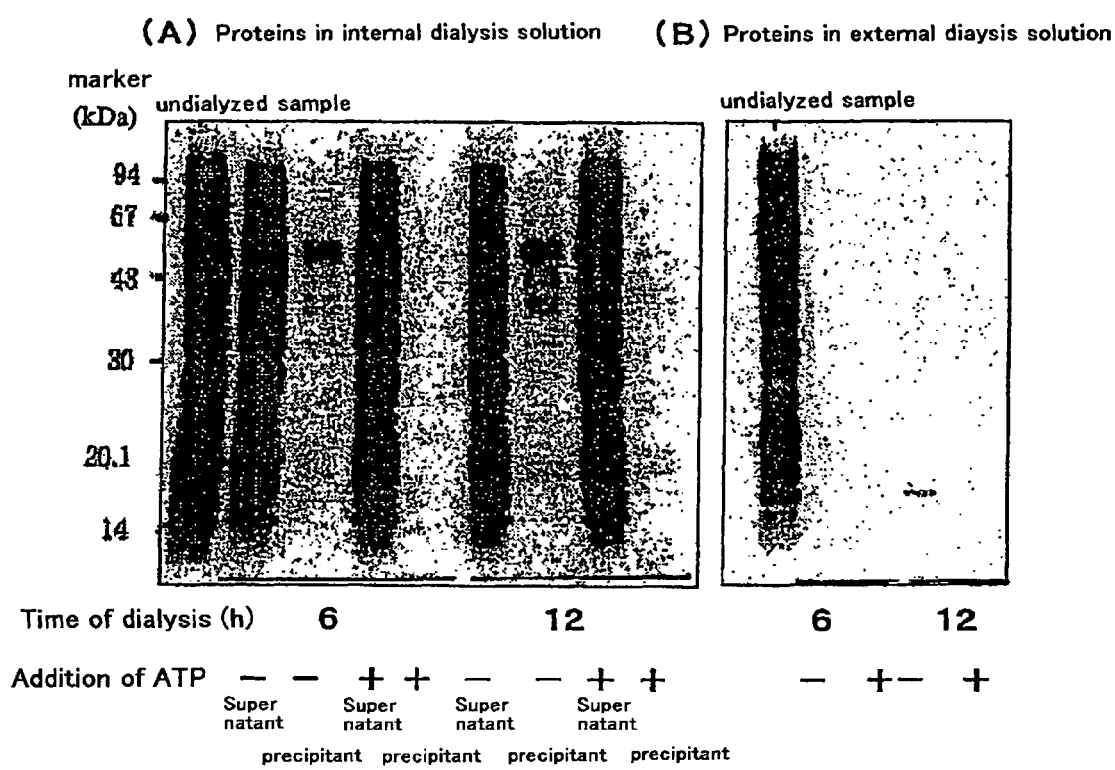
FIG. 2 is an electrophoresis profile showing the SDS-polyacrylamide gel electrophoresis protein analysis results of soluble proteins and insoluble proteins in the dialysis membrane, in the presence and in the absence of ATP.

(3) Analysis of Insoluble Proteins and Soluble Proteins Resulting from Dialysis in the Absence of ATP The soluble and insoluble fractions obtained above in (2) at six hours and 12 hours of dialysis were separated by SDS polyacrylamide gel electrophoresis (SDS-PAGE) and stained with Coomassie Brilliant Blue (CBB). The results are shown in FIG. 2. In the figure, (A) shows the results using samples from the internal dialysis solution and (B) shows the results using samples from the external dialysis solution. The far left-hand column is a molecular weight marker, to the right of which are shown the extract solutions before dialysis was performed. The minus sign indicates extract solution 1, to which ATP was not added, and the plus sign indicates extract solution 2, to which ATP was added. Furthermore, the fractions obtained by centrifugation as described above in (2) are indicated as supernatant and precipitate.

As is made clear by the figure, a prominent difference is not observed in the soluble protein (supernatant) component, according to the presence or absence of ATP, but a marked difference was seen for the insoluble fraction (precipitate). While a number of protein bands can be seen around 50,000 D for insoluble proteins produced in the absence of ATP, no CBB positive protein bands were detected for insoluble proteins in the presence of ATP.

In terms of proteins in the external dialysis solution, after collecting the external dialysis solution, these were precipitated with 10% trichloroacetic acid and recovered, and then analyzed with SDS-PAGE. The results (FIG. 2(B)) showed that, after 12 hours, a trace amount of low molecular weight substances in the external dialysis solution were detected to have migrated to the edge of the gel at around 14,000 D.

Furthermore, the amounts of protein in the external dialysis solution, as calculated by the densitometric method, with bovine serum albumin as the standard protein, were 7 µg (in the presence of ATP) and 23 µg (in the absence of ATP) per milliliter of dialysis sample. No significant difference was observed in the mass of the proteins eliminated by the dialysis that was performed as described above in (1) under either of the dialysis conditions. The fact that the difference in the amount of soluble protein before and after analysis was greater than the sum of the insoluble protein and the protein evacuated to the external dialysis solution in both experiments shows that protein adhered to the membrane during dialysis. However, considering that no difference was seen in the electrophoresis patterns of the protein bands before and after dialysis (comparison of the bands for the undialyzed sample and the supernatant proteins) it will be understood that it was not the case that specific molecular species of protein adhere to the dialysis membrane used in a specific manner.

(4) Measurement of Protein Synthesis Activity in Wheat Embryo Extract After Dialysis Wheat embryo extracts which had dialyzed as described above in (2) for 0, 2, 4, 6 and 12 hours, were used for protein synthesis. A known method for continuous wheat embryo cell-free protein synthesis (Endo, Y. et al, [1992] *J. Biotech.*, 25, 221-230; Madin, K. et al., *Proc. Natl. Acad. Sci. USA*, [2000] 97, 559-564) was followed with some modifications. That is to say, 25 µl of reaction solution for protein synthesis (20 mM of HEPES-KOH (pH7.6), 95 mM of potassium acetate, 2.65 of mM magnesium acetate, 0.380 mM of spermidine (Nacalai Techtonics), 0.3 mM of each of the 20 types of L-amino acids, 4 mM of dithiothreitol, 1.2 mM of ATP (Wako Pure Chemical), 0.25 mM of GTP (Wako Pure Chemical), 16 mM of creatine phosphate (Wako Pure Chemical), 1 U/µl of RNase inhibitor (TAKARA), 0.5 µg/1 of creatine kinase (ROCHE), and 1 µg of translation template mRNA (Ω GFP), at final concentrations) containing 6 µl of the solution containing wheat embryo extraction product, which was prepared by dialysis as described above, was placed in a dialysis membrane, and the reaction was performed for 48 hours at 26° C. in a system wherein this was dialyzed against 10 volumes of external dialysis solution (20 mM of HEPES-KOH, pH 7.6, 95 mM of potassium acetate, 2.65 mM of magnesium acetate, 4 mM of dithiothreitol, 1.2 mM of ATP, 0.25 mM of GTP, 16 mM of creatine phosphate, 0.5 mg/ml of creatine kinase, 0.380 mM of spermidine, the 20 types of L-amino acids (0.3 mM each), and 0.005% of $NaN_3$). A SPECTRA/PORE 6 (Spectrum Laboratories Inc., CA, USA) having a molecular weight cutoff of 50,000 was used as the dialysis membrane.

To produce the mRNA (Ω GFP) serving as the translation template, using GFP/pEU plasmid (WO01/27260) that contains the tobacco mosaic virus (TMV) Omega (Ω) sequence, a translation initiation factor, ligated to SP6 promoter and GFP DNA ligated downstream of the 3'-end as a template, transcription was performed with SP6 RNA polymerase (TOYOBO), and the resulting RNA was phenol/chloroform extracted, ethanol precipitated, and then purified with a Nick Column (AMERSHAM Pharmacia Biotech).

Figure 3:
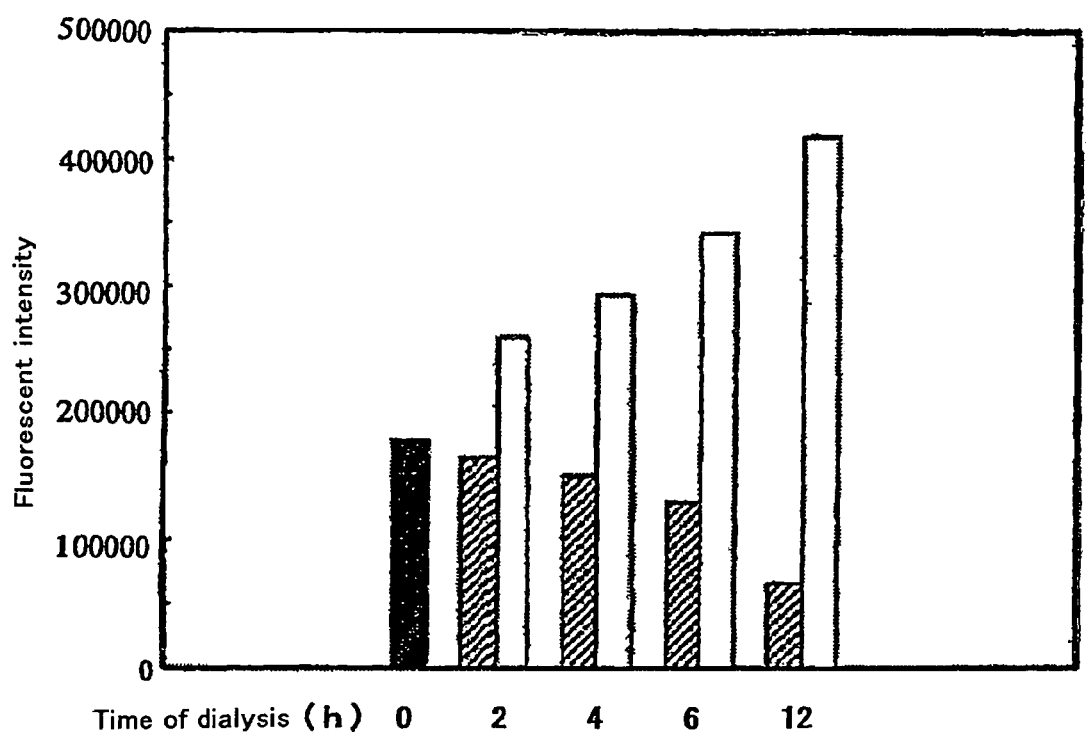
FIG. 3 is a graph showing the protein synthesis activity of cell extracts (after dialysis) produced by dialysis in the presence or in the absence of ATP.

After the reaction had ended, the protein in the synthesis reaction solution was separated by SDS polyacrylamide gel electrophoresis, stained with Coomassie Brilliant Blue and quantified according to the method described in the manuscript of Endo et al. (Madin, K. et al., *Proc. Natl. Acad. Sci. USA*, 97, 559-564 [2000]). The GFP activity was quantified by measuring the fluorescent intensity using a TD-360 MINI FLUOROMETER by TURNER DESIGNS, according to the manufacturer's instructions. The results are shown in FIG. 3.

As can be understood from the figure, the wheat embryo extract sample produced by dialysis in the presence of ATP (white bar) showed enhanced protein synthesis with increasing dialysis time, reaching 236% of the undialyzed sample (black bar) at 12 hours of dialysis. Meanwhile, the sample that was dialyzed in the absence of ATP (diagonally shaded bar) showed a marked drop in protein synthesis activity, and was found to drop to 37.5% of the protein synthesis activity of the undialyzed sample at 12 hours of dialysis.

From the foregoing results it was understood that, while protein synthesis activity could be markedly increased by using wheat embryo extract from which low molecular weight synthesis inhibitors had been removed, if the low molecular weight synthesis inhibitors were removed by dialysis, a drop in protein synthesis activity was provoked by insolubilization in the solution. It was also understood that this insolubilization in the solution could be prevented by adding ATP, and that when dialysis was performed while preventing insolubilization, protein synthesis activity was enhanced. Next, as a first step to understanding the mechanism behind the insolubilization phenomena in the internal dialysis solution at the molecular level, attention was focused on RNA, which, from among the components of the wheat embryo extract, is a primary factor in protein synthesis, thus the components of the insoluble fraction were analyzed.

Example 3

Analysis of the Insoluble Fraction

Figure 4:
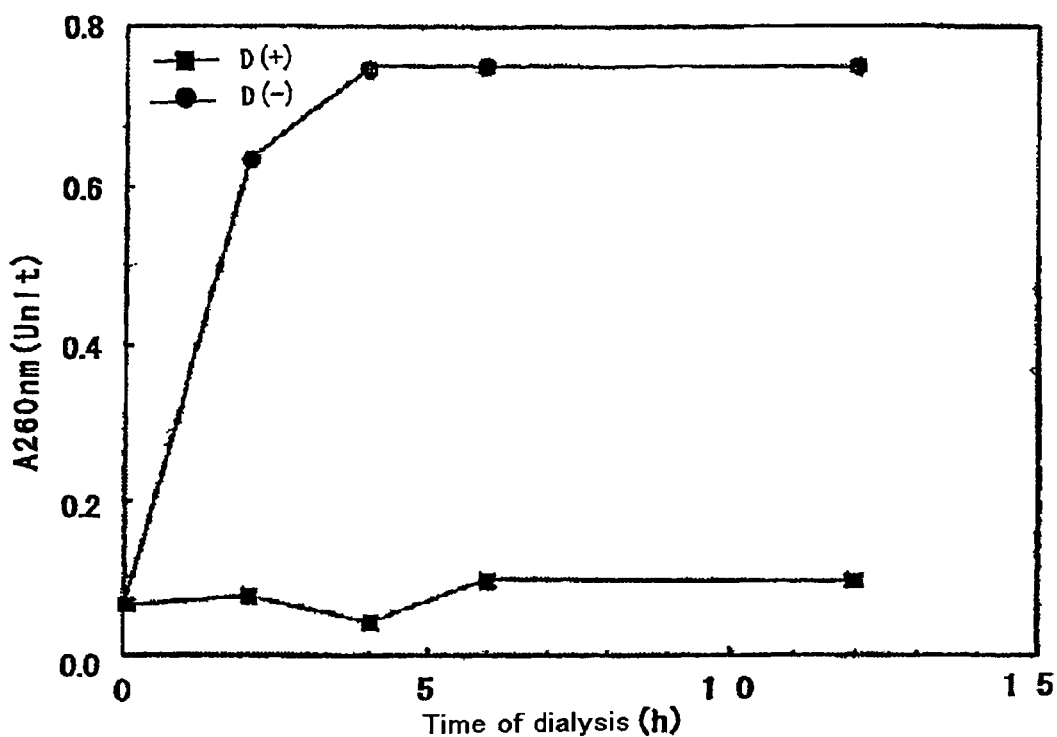
FIG. 4 is an electrophoresis profile and a graph showing the results of quantitative and qualitative analysis of nucleic acid components, and particularly RNA, in the insoluble matter formed by dialysis.
Figure 4:
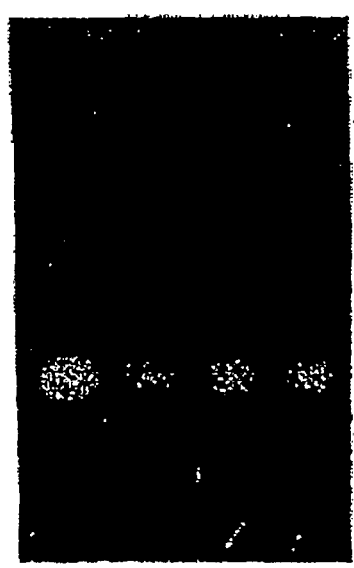
Figure 4:
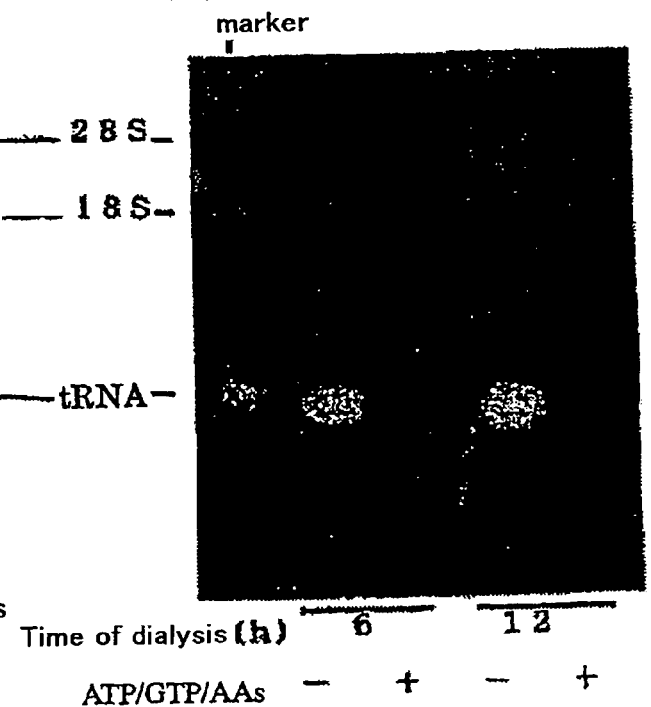

Nucleic acids were extracted from the insoluble fraction produced in Example 2 (2) described above, by the SDS-phenol method. The methods for this RNA extraction, the quantification and the analysis by means of gel electrophoresis were the methods described in the manuscript of Endo et al. (Endo, Y. et al., *J. Biotech.*, 25, 221-230 [1992]). The results are shown in FIG. 4. The amount of nucleic acids was measured by ultraviolet absorption (A260 nm). As can be understood from the figure, with the wheat embryo extract produced by dialysis in the presence of ATP (the line indicated by the solid squares in FIG. 4A) only trace amounts of nucleic acid were detected, while the wheat embryo extract solution produced by dialysis in the absence of ATP (the line indicated by the solid circles in FIG. 4A) contain high concentrations of nucleic acids. Since this insolubilization in the solution containing these nucleic acids continues for 4 hours after the start of dialysis, it may be asserted that the kinetics thereof are different from those of protein insolubilization for which the value was constant after two hours (see FIG. 1A).

Furthermore, when ultraviolet absorbing material, which was extracted from the insoluble matter formed by the wheat embryo extract after six hours of dialysis, was analyzed by agarose gel electrophoresis, positive ethidium bromide staining, and mobility with respect to the marker band confirmed that the primary component was tRNA (FIG. 4B, lane [−]). Based on these facts, the phenomenon wherein protein synthesis activity is greatly reduced as a result of dialysis in the absence of ATP can be explained by the formation of insoluble matter containing tRNA by some mechanism, which results in a specific drop in the concentration of tRNA in the wheat embryo extract. Each milliliter of undialyzed sample contains approximately 10 $A_{260}$ nm units of tRNA and, considered in light of the fact that a transition of less than 8% of the tRNA to insoluble matter reduces protein synthesis by 30% (6 hours of dialysis, FIG. 3), it is possible that the tRNA contained in this insoluble matter may be a specific molecular species that recognizes certain codons on mRNA. In any case, the experimental results (+ATP lane) have made it possible to confirm that ATP functions as an insolubilization inhibitor in the reaction wherein such insoluble matter containing tRNA is formed. It has been reported that tRNA within the cell, aminoacyl-tRNA, does not exist in its free state, but forms a complex with aminoacyl-tRNA synthetase, 5SrRNA and some ribosome proteins (M. Mirande, et al., Eur. J. Biochem. 147, 281-289 [1985]; K.Ogata et al., J. Biochem., 110, 1037-1044 [1991]). When further considered in light of these reports, the experimental results shown here suggest that ATP is involved in the formation of this complex. Here, in order to determine whether or not the effect of preventing insolubilization and activating protein synthesis activity in wheat embryo extract during dialysis was a phenomena specific only to ATP, the following studies were made.

Example 4

Investigation of Factors Preventing the Formation of Insoluble Matter (Factors Inducing Stability in the Extract Solution) During the Elimination of Low Molecular Weight Substances From Wheat Embryo Extract, using a Dialysis Membrane, and Factors Inhibiting Inactivation of Protein Synthesis (1) Analysis of Factors Inducing Stability in the Extract Solution In order to analyze whether or not the effect of preventing the formation of insoluble matter during dialysis was specific to ATP, in the dialysis performed in Example 2 (1), an extract solution 3 was prepared by adding 0.25 mM of GTP to the extract solution 1 described in Example 2 (1); and extract solution 4 was prepared by adding the 20 types of L-amino acids (0.3 mM each) to extract solution 1; and an extract solution 5 was prepared by adding 1.2 mM of ATP, 0.25 mM of GTP and the 20 types of L-amino acids (0.3 mM each) to extract solution 1.

Figure 5:
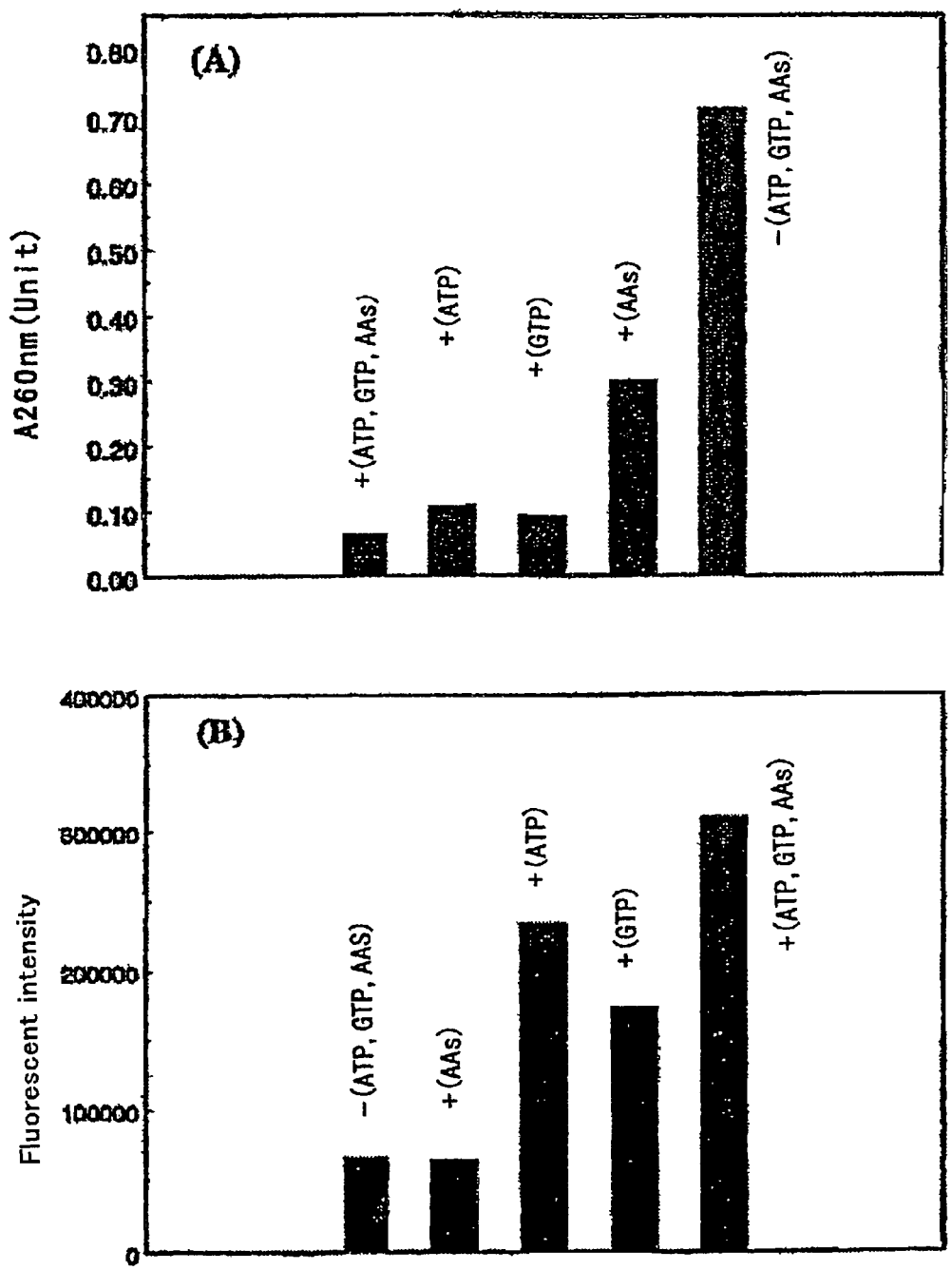
FIG. 5 is a graph illustrating quantification of nucleic acid components (RNA) in the insoluble matter after dialysis, and the protein synthesis activity of the soluble fraction.

Using these extract solutions, dialysis was performed for six hours by the same method as described in Example 2 (1) and the nucleic acids in the insoluble fraction were analyzed in the same manner as in Example 3. The results are shown in FIG. 5(A). As can be understood from the figure, the effect of adding GTP (+[GTP]) in terms of preventing the insolubilization of nucleic acids (tRNA) in the wheat embryo extract after six hours of dialysis was approximately equal to that of ATP (+(ATP)), and while the effect was lower than that of ATP and GTP, amino acids (+(AAs)) also had an effect.

(2) Measurement of Protein Synthesis Activity in Wheat Embryo Extract After Dialysis The wheat embryo extract obtained above in Example 4(1) was used for protein synthesis in the same manner as in Example 2(3) with GFP mRNA as the template, and the amount of protein synthesized was likewise measured by way of fluorescent intensity. The results are shown in FIG. 5(B). The insolubilization prevention effect of GTP (+(GTP)) was approximately the same, and it was determined that protein synthesis was enhanced to approximately the same degree as with ATP (+(ATP)). However, while amino acids (+(AAs)) do show a certain degree of tRNA insolubilization prevention effect, almost no effect was observed in terms of enhancing protein synthesis activity. Furthermore, it was determined from these experiments that wheat embryo extract dialyzed in the co-presence of ATP, GTP and the 20 types of amino acids had the lowest amount of insoluble matter (tRNA) (FIG. 5(A) (+(ATP, GTP, AAs)) and, at the same time, the highest protein synthesis activity (FIG. 5(B) (+(ATP, GTP, AAs)). Furthermore, the formation of insoluble matter (tRNA) was not detected, even after 12 hours of dialysis (FIG. 4C).

The foregoing results indicate that, in addition to ATP, GTP and amino acids are also involved in the insolubilization of tRNA, and at the same time these insolubilization prevention effects are not the direct cause of the effect of enhancing protein synthesis through dialysis. Furthermore, it was made clear that the effect of enhancing protein synthesis through dialysis of wheat embryo extract is most effective when this is performed in the co-presence of ATP, GTP and the 20 types of amino acids.

Comparative Example 1

Study of the Effects on Protein Synthesis Activity of Stationary Operations in the Co-Presence of ATP, GTP and the 20 Types of Amino Acids The following experiment was performed in order to confirm that the effect (Example 4) whereby the protein synthesis activity of wheat embryo extract produced by dialysis in the co-presence of ATP, GTP and the 20 types of amino acids is enhanced was not achieved by simple static operations in the presence of ATP, GTP and the 20 types of amino acids.

Figure 6:
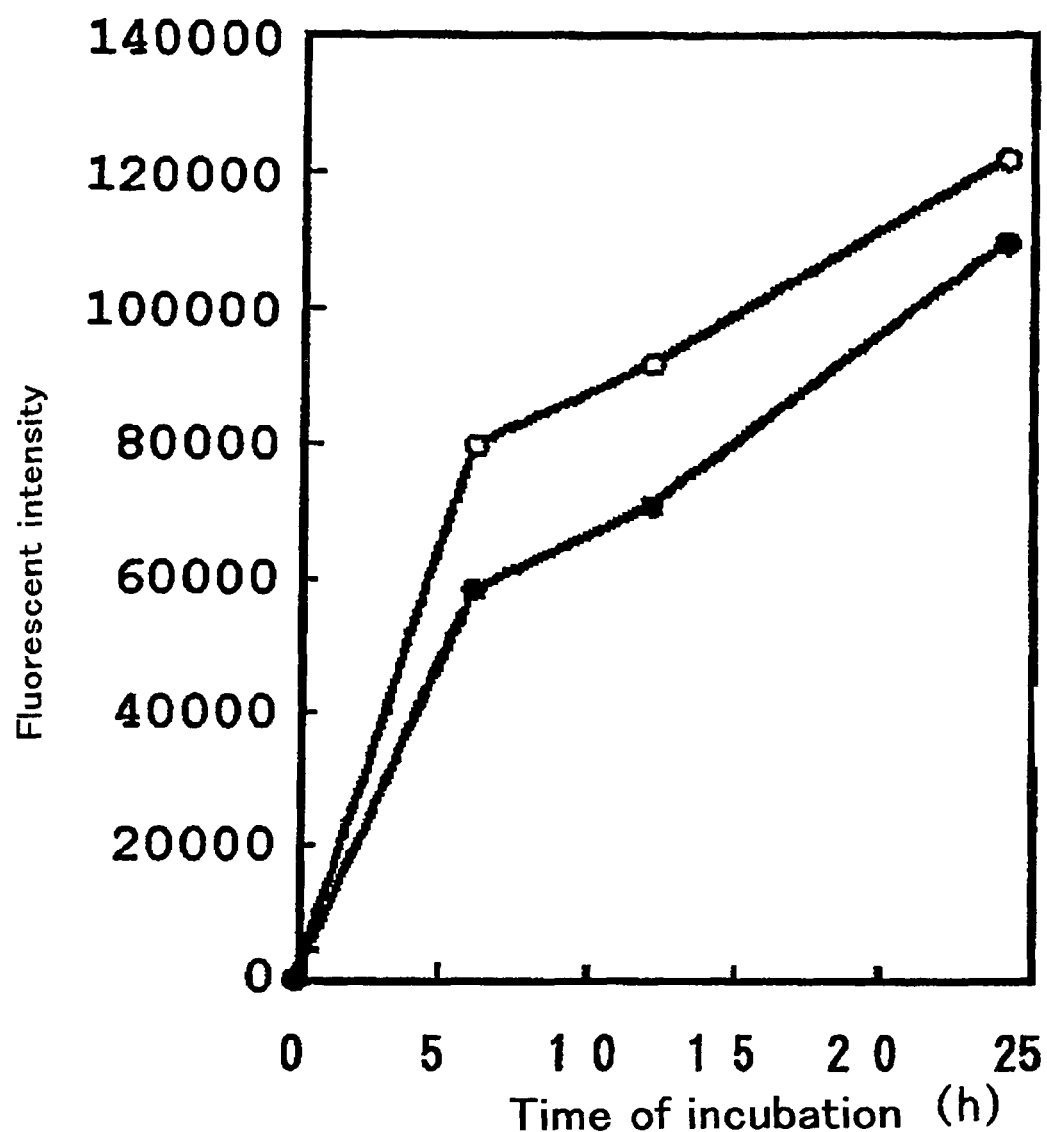
FIG. 6 is a graph showing the effect on protein synthesis activity of adding stabilizing components in the batch method.

The extract solution 5 (wherein all of the factors necessary for protein synthesis, these being 1.2 mM of ATP, 0.25 mM of GTP, the 20 types of L-amino acids [0.3 mM each] were added to wheat embryo extract) described in Example 4(1) was left to stand for six hours at 26° C., which were the same conditions as for dialysis. Thereafter, it was used for protein synthesis in the same manner as in Example 2(3) with GFP mRNA as the template, and the amount of protein synthesized was likewise measured by way of fluorescent intensity. The results are shown in FIG. 6. In the figure, the line indicated by the solid circle shows the results for the extract solution for which the operation described above was performed, and the line indicated by the empty circle indicates the results of a conventional method wherein the operation described above was not performed. As can be understood from the figure, no protein synthesis enhancement effect was observed as a result of the operation described above, rather a decrease in protein synthesis activity was seen. Based on this, it can be asserted that the enhancement of protein synthesis activity through dialysis in the co-presence of ATP, GTP and amino acids, is not simply the result of allowing this to stand in the co-presence of these factors, but results from the removal of low molecular weight substances by the dialysis membrane.

It has already been reported, with regard to the effect on protein synthesis activity of the operations described above, that a cell-free protein synthesis reaction using wheat embryo extract synthesizes a markedly greater amount of protein as a result of performing operations by way of a batch reaction method wherein the reaction is performed in the stationary state for 30 minutes at 30° C. in the presence of components necessary to protein synthesis, such as ATP, GTP and amino acids (Y. Shuiliang et al., J. Ferment. Bioeng. 84, 548-552, [1997]). On the basis of these results, the authors surmised that the effects of the ATP, GTP and amino acids were: (i) the formation/accumulation of an initiation factor-2.GTP.aminoacyl-tRNA ternary complex (eIF-2.GTP.aminoacyl-tRNA); and (ii) the formation/accumulation of a 43S pre-initiation complex. The results shown in the example described above demonstrated that dialysis for long periods of time enhances protein synthesis activity, even in the presence of ATP or GTP alone. It is known that, in the initiation stage of the protein synthesis reaction, GTP is necessary for the reaction that forms the 43S pre-initiation complex, but ATP is not necessary. Considering that the present experiment showed that the dialysis operation enhanced protein synthesis activity in the presence of ATP alone, this suggests that our findings are the result of a different mechanism than that which had previously been reported (Y. Shuiliang et al., *J. Ferment. Bioeng.* 84, 548-552, [1997]).

Example 5

Figure 7:
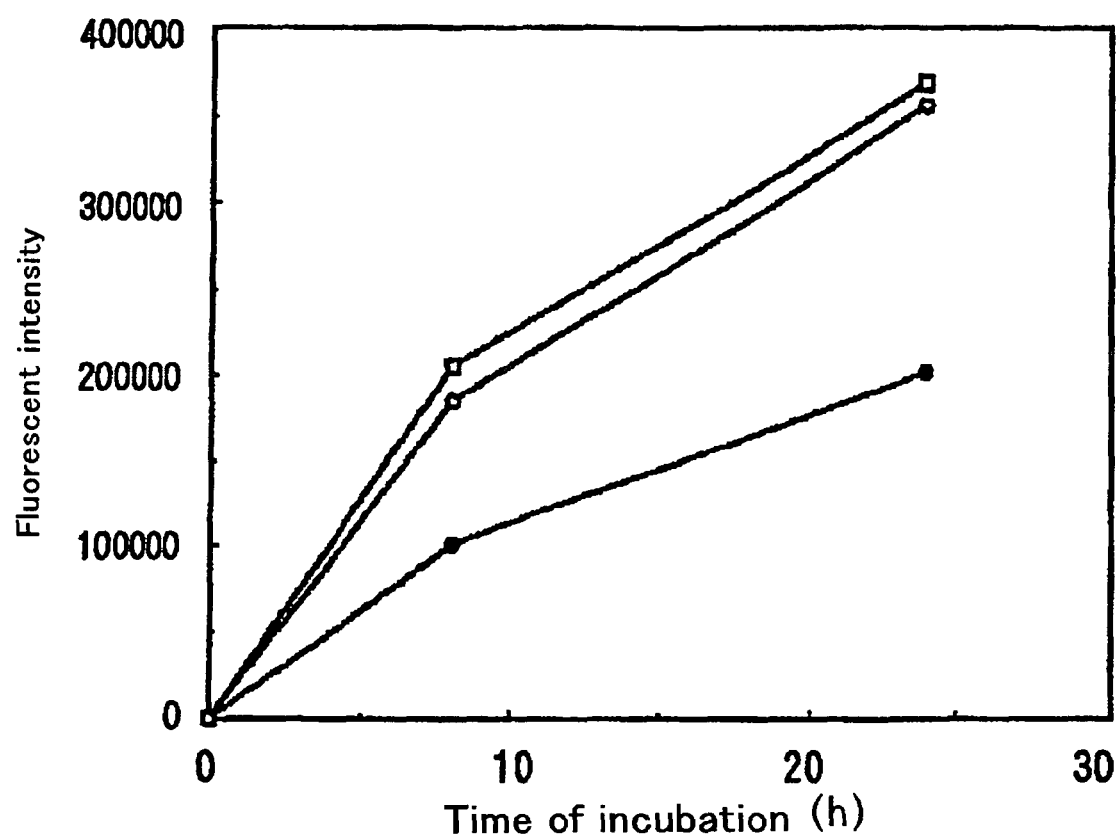
FIG. 7 is a graph showing the temperature dependency of the effect of enhancing protein synthesis resulting from dialysis of the cell extract.

Study of the Temperature Dependency of Protein Synthesis Activity During Dialysis The temperature dependency of the effect of enhancing protein synthesis activity through dialysis of wheat embryo extract, which was observed in Example 2(4) and Example 4(2), was analyzed. The extract solution 5 (wherein all of the factors necessary for protein synthesis, these being 1.2 mM of ATP, 0.25 mM of GTP, and the 20 types of L-amino acids (0.3 mM each) were added to wheat embryo extract) described in Example 4(1) was dialyzed for six hours at 4° C. and 26° C., whereafter, it was used for protein synthesis in the same manner as in Example 2(3) with GFP mRNA as the template, and the amount of protein synthesized was likewise measured by way of fluorescent intensity. Furthermore, the extract solution 5 was simply left to stand for six hours at 4° C., in the same manner as in the comparative example described above, as a control experiment. The results are shown in FIG. 7.

As compared with the results (solid circles) for the wheat embryo extract produced by stationary operations at 4° C., as a control, results for dialysis at 4° C. (empty circles) and results for the same at 26° C. (empty squares) showed that approximately twice the protein synthesis activity was maintained. Furthermore, it was shown that, even when the dialysis temperature was 4° C., approximately the same or better enhancement effect was provided, as compared to that at 26° C. From these findings, it is judged that the phenomenon of enhancing protein synthesis activity that is seen in dialyzing wheat embryo extract for long periods of time in the presence of ATP and the like directly involves not a biochemical reaction, but the physical effect of the dialysis membrane (removal of low molecular weight synthesis inhibitors).

In other words, low molecular weight translation inhibitors or nonspecific blockers are present in the wheat embryo extract, and the phenomenon of enhancing protein synthesis activity is shown to be caused by the elimination of these from the group of translation factors through dialysis. Meanwhile, if dialysis is performed at 4° C. in the absence of ATP or the like, insoluble matter forms. This shows that, even at 4° C., ATP and the like are important in stabilization, and particularly in the stabilization over long periods of time, of translation factors.

On what principle is the effect of enhancing protein synthesis activity when dialysis of wheat embryo extract is performed for long periods of time in the presence of ATP based? In the examples described above, the present inventors have shown: (i) that no remarkable difference is observed in the molecular species of soluble protein in wheat embryo extracts produced by dialysis in the presence or in the absence of ATP (results shown in FIG. 2A); and (ii) that the effect of enhancing protein synthesis activity is observed even through dialysis at 4° C. (FIG. 7). The findings suggest that low molecular weight substances which inhibit or block the translation reaction are present in wheat embryo extract.

Example 6

Analysis of the Influence of Low Molecular Weight Synthesis Inhibitors on Protein Synthesis Activity A great variety of low molecular weight substances, including unidentified substances, were present in the wheat embryo extract produced as a supernatant by centrifuging at 30,000×g, as described in Example 1. In fact, this could also be visually confirmed as containing a high concentration of yellow colored low molecular weight substances. Normally, gel filtration operations were performed on the centrifugation supernatant, in order to eliminate low molecular weight substances, such as amino acids and nucleotides. However, in none of the reported methods (Madin, K. et al., *Proc. Natl. Acad. Sci. USA*, (2000) 97, 559-564, JP-2000-236896-A and the like) have extensive attempts been directed at the complete elimination of such low molecular weight substances. That is to say, research has not been performed with a view to investigating the effect of protein synthesis inhibitors in the low molecular weight fraction from this point of view. Here, in order to study this possibility, the following experiment was performed.

Specifically, 400 µl of wheat embryo sample obtained by limited grinding using a WARING Blender, as in Example 1, was centrifuged at 30,000×g, the supernatant obtained was subject to gel filtration in a 4 ml capacity SEPHADEX G25 column, and the low molecular weight fraction retained in the column (including substances having molecular weights of no greater than 5,000) was eluted and once again subject to gel filtration in the same manner to produce yellow low molecular weight substance fraction. After freeze-drying this, it was dissolved in 40 µl of 10 mM HEPES-KOH at pH 7.6 and added to a batch type cell-free protein synthesis system (total reaction capacity; 80 µl).

In other words, as in the method already described in Example 2(1), using a protein synthesis solution (with GFP mRNA as a template) containing wheat embryo extract, which had been dialyzed for 12 hours in the presence of ATP, the influence of low molecular weight substances on protein synthesis was investigated using the batch reaction method. The preparation of the reaction solution and the reaction method were, with some modifications, in accordance with an existing report (Madin, K. et al., *Proc. Natl. Acad. Sci. USA*, 97, 559-564 [2000]). A solution containing 30 mM of HEPES-KOH (pH7.6), 6.95 mM potassium acetate, 2.65 mM of magnesium acetate, 2.85 mM of dithiothreitol, 1.2 mM of ATP, 0.25 mM of GTP, 16 mM of creatine phosphate, 0.5 mg/ml of creatine kinase, 0.380 mM of spermidine, the 20 types of L-amino acids (0.3 mM each), and 1,000 units/ml of ribonuclease inhibitor (RNasin) was used for the reaction solution. The GFP mRNA described in Example 2(4) was added in the amount of 60 µg/ml and the reaction was performed at 26° C.

Figure 8:
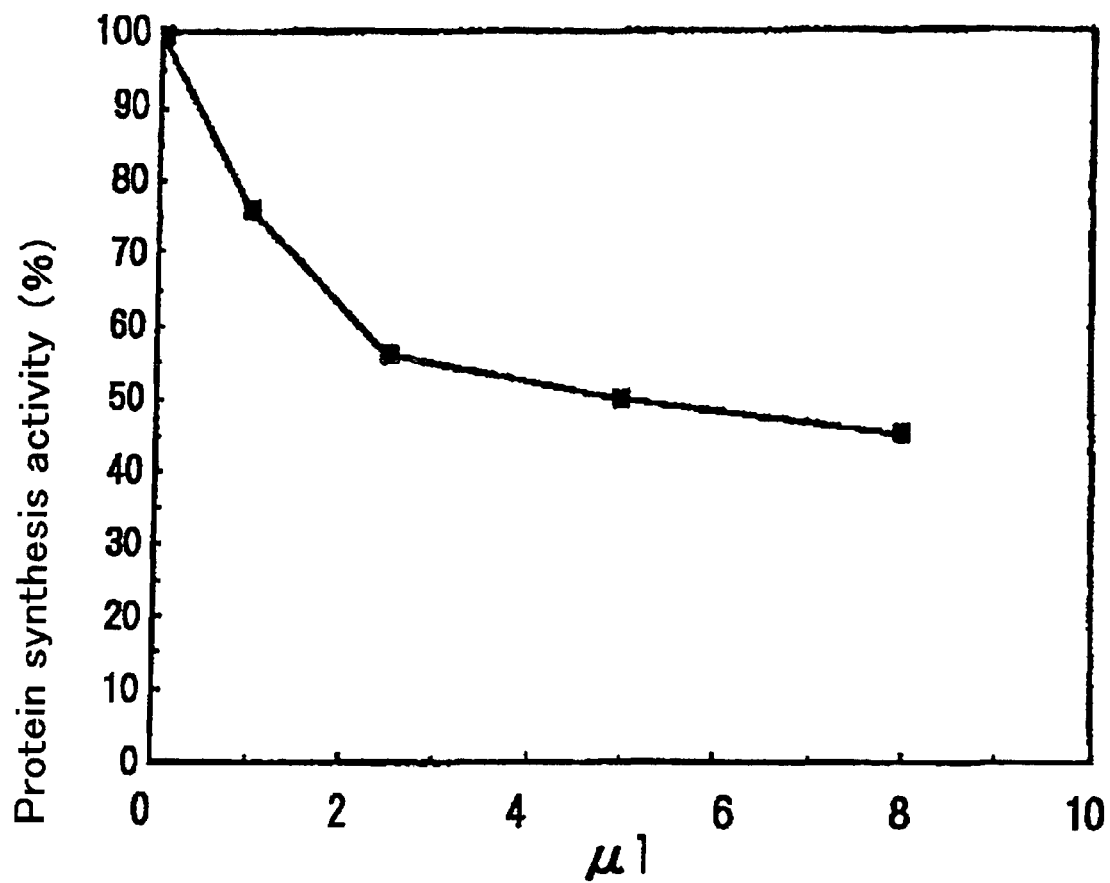
FIG. 8 is a graph illustrating the protein synthesis inhibitory effect of substances contained in wheat embryo, fractionated with a SEPHADEX G25 column.

The results are shown in FIG. 8. In the figure, the horizontal axis is the volume of the yellow low molecular weight fraction added. Protein synthesis activity was measured based on the radioactive count of the [$^{14}$C] leucine incorporated into the protein in two hours at 26° C. Here, a radioactive count of 3,600 dpm incorporated into the protein in 5 µl of reaction solution was taken as 100%.

As shown in FIG. 8, it was found that protein synthesis was strongly inhibited in accordance with the amount of this low molecular weight substance fraction containing yellow substances that was added. In other words, while the mechanism of inhibition is unclear, it was shown that the protein synthesis activity inhibiting factor was present in the low molecular weight fraction contained in the wheat embryo extract. With consideration for these findings and such experimental results as the phenomena of enhancing protein synthesis activity, as described above, the following explanation can be established. That is to say, by dialyzing wheat embryo extract in the presence of such insolubilization inhibitors as ATP, low molecular weight factors inhibiting protein synthesis are eliminated from the wheat embryo extract by the dialysis membrane, as a result of which protein synthesis activity increases. With this approach, it is possible to explain the effect of preventing insolubilization brought about by ATP, GTP and the 20 types of amino acids (tRNA insolubilization) and the effect of promoting protein synthesis brought about by dialysis, as separate phenomena.

In terms of the mechanism of eliminating the low molecular weight substances that inhibit protein synthesis from the wheat embryo extract, this may possibly be explained, not in terms of transfer to the external dialysis solution, but as elimination by way of absorption by the dialysis membrane. The protein synthesis inhibitors shown here are included in the fraction absorbed by the SEPHADEX G25 column, and are also included in the substances eliminated by the SPECTRA/PORE 6, having a molecular weight cutoff of 50,000 Daltons, or by the regenerated cellulose membrane having a molecular weight cutoff of 12,000 to 14,000 Daltons. It is, therefore, probable that these have molecular weights of less than approximately 14,000 Daltons.

Example 7

Study of Wheat Embryo Extracts Containing all the Components Necessary for Protein Synthesis, Other Than a Template Various products are already marketed, wherein a cell-free protein synthesis reaction solution, using wheat embryo, is provided in a kit. However, all of these products store the wheat embryo extract and solutions containing amino acids, energy sources, ions, and the like in separate containers, and these components must be mixed with the template suitable to the purpose at when the protein synthesis reaction is performed. These mixing operations were difficult, for such reasons as the necessity of performing them at the low temperature of 0 to 4° C., which resulted in failures in the synthesis reaction. Furthermore, the constitution of such protein synthesis reaction kits is not suited for comprehensive synthesis of proteins from a multiplicity of genes and this problem of complex processes must be solution for future fully-automated robotization.

The extract solution 5 described in Example 4(1) contains, in addition to wheat embryo extraction product, ATP, GTP and amino acids. By performing dialysis in the co-presence of these factors, it was possible to prepare a wheat embryo extract having much higher protein synthesis capacity than was conventional (FIG. 5B). Thus, using a sample wherein, prior to dialysis, the concentrations of the various constituent components were brought to optimal concentrations for cell-free protein synthesis using the wheat embryo extract, it should be possible to perform cell-free protein synthesis easily, simply by adding mRNA to this solution after dialysis.

Figure 9:
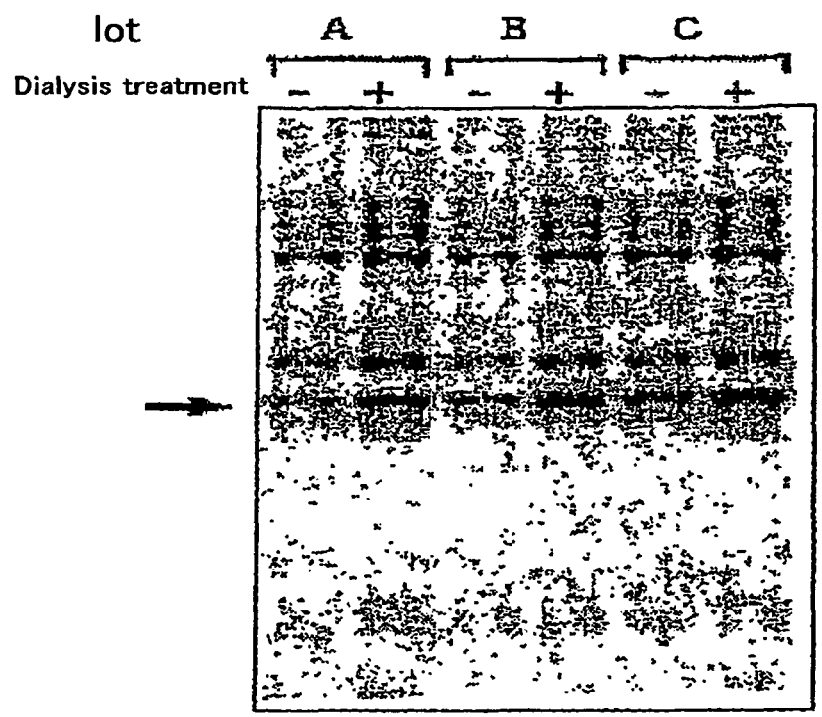
FIG. 9 shows an electrophoresis profile and graphs illustrating the performance of a ready-made cell extract derived from wheat embryo.
Figure 9:
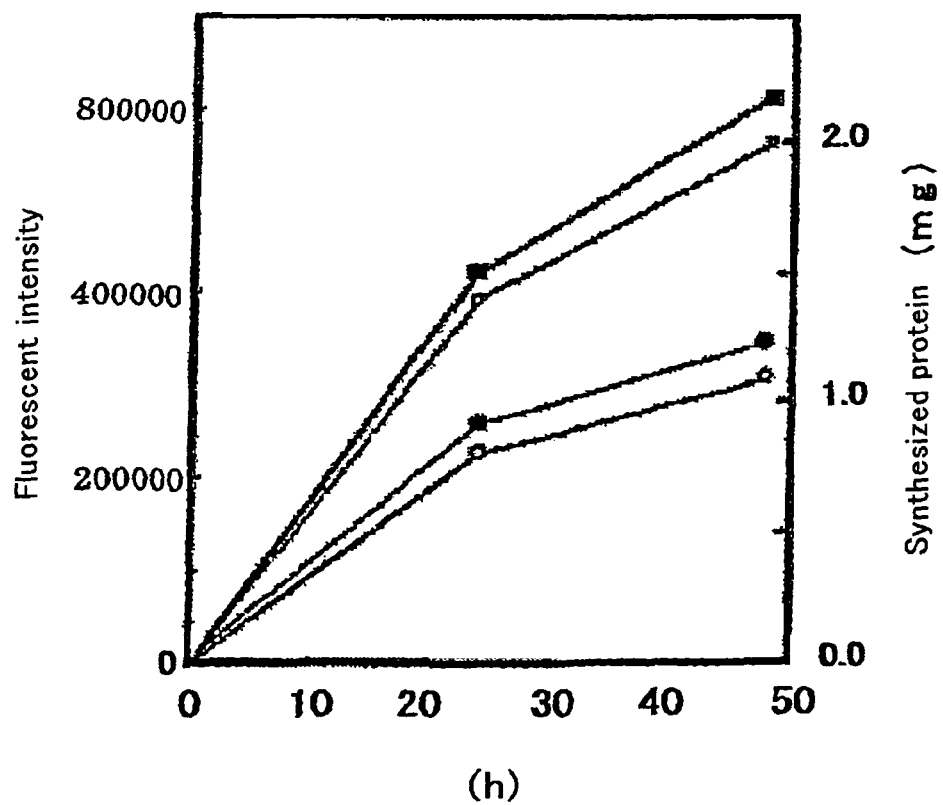

Three lots of different types of wheat embryo extract obtained by the method of Example 1 were prepared with the composition of extract solution 5, as described in Example 4(1), and these were dialyzed for 12 hours by the method described in Example 2(1). These extract solutions were used in a continuous method using a dialysis membrane, with the GFP mRNA as template, in the same manner as the method described in Example 2(4), and the protein synthesis activity of dialyzed and undialyzed wheat embryo extracts were measured. The results are shown in FIG. 9. FIG. 9A shows the results of analysis of the samples after 48 hours of protein synthesis reaction, using SDS-polyacrylamide gel electrophoresis, and the arrow shows the Coomassie Brilliant Blue stained bands for the GFP produced. It was understood that, whether the extract solutions from lot A, B or C were used, the amount of GFP synthesized using the wheat embryo extract that had undergone dialysis (dialysis [+]) was much greater than that with the wheat embryo extract which had not undergone dialysis (dialysis[−]). The graph in FIG. 9B shows the amount of protein synthesized for each milliliter of reaction solution, calculated by densitometry, using a standard sample of purified GFP as a reference. It is understood that the solution that was subject to dialysis (solid squares) had approximately two times the synthesis capacity of the solution that was not subject to dialysis (solid circles). Furthermore, the results of measuring the activity of the synthesis product from the fluorescent intensity of the GFP confirmed that both the wheat embryo extract that was subject to dialysis treatment (empty squares) and the wheat embryo extract that was not subject to dialysis treatment (empty circles) possess a similar specific enzyme activity. In other words, it was shown that the capacity for higher order structure formation of the synthesis product was not lowered by this dialysis operation.

Furthermore, after storing the high-function wheat embryo extract prepared in this manner at −80° C. for more than four weeks and performing the same analysis of protein synthesis activity, no drop in this activity was observed, as compared with the activity immediately after preparation. Furthermore, in terms of the dialysis membrane used for dialysis and continuous protein synthesis, when a regenerated cellulose membrane having a molecular weight cutoff of 12,000 to 14,000 Daltons was used in place of the SPECTRA/PORE 6 having a molecular weight cutoff of 50,000 Daltons, it was possible to achieve approximately the same experimental results.

Possibilities for Industrial Use

According to the present invention, low molecular weight substance that inhibit protein synthesis are eliminated from cell extract used in cell-free protein synthesis systems, making it possible to obtain a cell extract having enhanced protein synthesis activity. Furthermore, by performing the process of eliminating low molecular weight inhibitors from the cell extract in the presence of all of the components necessary for protein synthesis, with the exception of the translation template, a ready-made cell extract can be provided.

The present application is based on Japanese Patent Application 2002-23141, the entire contents of which are incorporated herein.

The invention claimed is:

1. A plant embryo extract with protein synthesis activity, wherein an endosperm component that contaminates the embryo extract and a low molecular weight substance that inhibits protein synthesis are removed from said embryo extract, wherein the embryo extract does not have added translation template, wherein the low molecular weight substance has a molecular weight of no greater than 14,000 Daltons, and wherein the removal of the low molecular weight substance is performed in the presence of exogenously added ATP, exogenously added GTP, and exogenously added amino acids.

2. The plant embryo extract of claim 1, wherein the low molecular weight substance having a molecular weight no greater than 14,000 Daltons that inhibits protein synthesis is removed by dialysis, using a regenerated cellulose membrane having a molecular weight cutoff of 12,000 to 14,000 Daltons.

3. The plant embryo extract of claim 1, wherein the plant embryo extract is substantially free of insoluble matter.

4. The plant embryo extract of claim 1, wherein the plant embryo extract is a wheat embryo extract.

5. A method for making a plant embryo extract for cell-free protein synthesis, wherein the plant embryo extract has protein synthesis activity and, wherein said plant embryo extract does not have added translation template, comprising:
removing, prior to protein synthesis, a contaminating endosperm component from a plant embryo extract, and a low molecular weight substance with a molecular weight of no greater than 14,000 Daltons, wherein the low molecular weight substance inhibits protein synthesis, and wherein the low molecular weight substance is removed in the presence of exogenously added ATP, exogenously added GTP, and exogenously added amino acids.

6. The method of claim 5, wherein the plant embryo extract is a wheat embryo extract.

7. A method for making a cell extract for cell-free protein synthesis, wherein said cell extract has protein synthesis activity, and wherein the cell extract does not have an added transition template, comprising:
removing a low molecular weight substance in the presence of exogenously added ATP, exogenously added GTP, and exogenously added amino acids; wherein the low molecular weight substance has a molecular weight of no greater than 14,000 Daltons and the low molecular weight substance inhibits protein synthesis from a cell extract.

8. The method of claim 5, wherein the low molecular weight substance that inhibits protein synthesis is removed by dialysis, using a regenerated cellulose membrane having a molecular weight cutoff of 12,000 to 14,000 Daltons.

9. The method of claim 5, wherein the protein synthesis inhibitor is removed by dialysis.

10. A plant embryo extract for cell-free protein synthesis, wherein the plant embryo extract has protein synthesis activity and, wherein said plant embryo extract does not have added translation template, obtained by:
removing, prior to protein synthesis, a contaminating endosperm component from a plant embryo extract, and a low molecular weight substance with a molecular weight of no greater than 14,000 Daltons, wherein the low molecular weight substance inhibits protein synthesis, and wherein the low molecular weight substance is removed in the presence of exogenously added ATP, exogenously added GTP, and exogenously added amino acids.

11. The plant embryo extract of claim 3, wherein the plant embryo extract is a wheat embryo extract.

12. The method of claim 7, wherein the low molecular weight substance that inhibits protein synthesis is removed by dialysis, using a regenerated cellulose membrane having a molecular weight cutoff of 12,000 to 14,000 Daltons.

13. The method of claim 7, wherein the protein synthesis inhibitor is removed by dialysis.

14. The plant embryo extract of claim 1, wherein the exogenously added ATP is present in an amount of from 100 $\mu$M to 0.5 mM, the exogenously added GTP is present in an amount of from 25 $\mu$M to 1 mM, and the exogenously added amino acids are present in an amount from 25 $\mu$M to 5 mM for each of 20 standard amino acids.

15. The method of claim 5, wherein the exogenously added ATP is present in an amount of from 100 $\mu$M to 0.5 mM, the exogenously added GTP is present in an amount of from 25 $\mu$M to 1 mM, and the exogenously added amino acids are present in an amount from 25 $\mu$M to 5 mM for each of 20 standard amino acids.

16. The method of claim 7, wherein the exogenously added ATP is present in an amount of from 100 $\mu$M to 0.5 mM, the exogenously added GTP is present in an amount of from 25 $\mu$M to 1 mM, and the exogenously added amino acids are present in an amount from 25 $\mu$M to 5 mM for each of 20 standard amino acids.

* * * * *